US009241951B2

(12) United States Patent
O'Sullivan et al.

(10) Patent No.: US 9,241,951 B2
(45) Date of Patent: Jan. 26, 2016

(54) OF GASTROINTESTINAL HEALTH, IMMUNITY AND PERFORMANCE BY DIETARY INTERVENTION

(75) Inventors: John T. O'Sullivan, Tralee (IE); Michael Gallagher, Milstreet (IE); John O'Doherty, Clane (IE); Torres Sweeney, Clane (IE)

(73) Assignee: BIOATLANTIS LTD, Tralee (IE)

( * ) Notice: Subject to any disclaimer, the term of this patent is extended or adjusted under 35 U.S.C. 154(b) by 849 days.

(21) Appl. No.: 13/321,412

(22) PCT Filed: May 21, 2010

(86) PCT No.: PCT/EP2010/003088
§ 371 (c)(1),
(2), (4) Date: Apr. 30, 2012

(87) PCT Pub. No.: WO2010/133359
PCT Pub. Date: Nov. 25, 2010

(65) Prior Publication Data
US 2012/0258930 A1    Oct. 11, 2012

(30) Foreign Application Priority Data

May 21, 2009    (IE) ..................................... 2009/0398

(51) Int. Cl.
*C08B 37/00*    (2006.01)
*A61K 31/716*    (2006.01)
*A61K 31/737*    (2006.01)
*A61K 36/02*    (2006.01)
*A61K 45/06*    (2006.01)

(52) U.S. Cl.
CPC ............. *A61K 31/716* (2013.01); *A61K 31/737* (2013.01); *A61K 36/02* (2013.01); *A61K 45/06* (2013.01); *C08B 37/0024* (2013.01)

(58) Field of Classification Search
None
See application file for complete search history.

(56) References Cited

U.S. PATENT DOCUMENTS

2009/0148414 A1    6/2009  O'Doherty et al.

FOREIGN PATENT DOCUMENTS

| DE | 202005000192 | | 4/2005 | | |
| JP | 2003-146888 | | 5/2003 | | |
| KR | 10-2008-0007698 | * | 1/2008 | ................ | A23L 1/30 |
| WO | 03/045414 | | 6/2003 | | |
| WO | 2007/057873 | | 5/2007 | | |
| WO | WO2013/008155 | * | 1/2013 | ............. | A61Q 19/08 |

OTHER PUBLICATIONS

Chen et al., "Effects of fermentation products of Ganoderma lucidum on growth performance and immunocompetence in weanling pigs" Archives of Animal Nutrition (2008) vol. 62 No. 1 pp. 22-32.*

Oliveria et al., "Effects of the polysaccharide b-glucan on clastogenicity and teratogenicity caused by acute exposure to cyclophosphamide in mice" Regulatory Toxicology and Pharmacology (2008) vol. 53 pp. 164-173.*
English Machine translation of foreign patent KR10-2008-0007698, published Jan. 2008.*
Search Report and Written Opinion, dated Dec. 3, 2010, corresponding to International Application No. PCT/EP2010/003088 (filed May 21, 2010), parent of the present application, 21 pp.
Bonomi et al., Appl No. PREV1996 98818274, (1995) XP-002600903, "The Use of Bacillus subtilis in Association with Enzyme Pool in the Feeding of Sows and Weaning Piglets (Experimental Contribution)," Abstract only, 1 pg.
Deville et al. (2004) "Laminarin in the Dietary Fibre Concept," J Sci Food Agric 84:1030-1038.
Gardiner et al. (2008) "Effect of *Ascophyllum nodosum* Extract on Growth Performance, Digestibility, Carcass Characteristics and Selected Intestinal Microflora Populations of Grower-Finisher Pigs," Anim Feed Sci Technol 141:259-273.
Højberg et al. (Jan. 2003) "Potential Rates of Fermentation in Digesta from the Gastrointestinal Tract of Pigs: Effect of Feeding Fermented Liquid Feed," Appl Environ Micro 69(1):408-418.
Ilsley et al. (2005) "Effect of Dietary Quillaja Saponin and Curcumin on the Performance and Immune Status of Weaned Piglets," J Animal Science 83:82-88.
Krakowski et al. (1999) "The Effect of Nonspecific Immunostimulation of Pregnant Mares with 1,3/1,6 Glucan and Levamisole on the Immunoglobulins Levels in Colostrum, Selected Indices of Nonspecific Cellular and Humoral Immunity in Foals in Neonatal and Postnatal Period," Veterinary Immunology and Immunopathology 68:1-11.
Lynch, et al. (2007) "Effects of Increasing the Intake of Dietary β-Glucans by Exchanging Wheat for Barley on Nutrient Digestibility, Nitrogen Excretion, Intestinal Microflora, Volatile Fatty Acid Concentration and Manure Ammonia Emissions in Finishing Pigs," Animal 1(6):812-819.
Lynch et al. (published online Dec. 16, 2009) "The Effect of Dietary *Laminaria*-Derived Laminarin and Fucoidan on Nutrient Digestibility, Nitrogen Utilisation, Intestinal Microflora and Volatile Fatty Acid Concentration in Pigs," J Sci Food Agric 90:430-437.

(Continued)

*Primary Examiner* — Eric Olson
(74) *Attorney, Agent, or Firm* — Lathrop & Gage LLP

(57) ABSTRACT

This invention relates to the improvement of gastrointestinal health, immunity and performance by direct dietary intervention with a composition comprising a glucan and/or a fucan, and relates in particular to the transfer of associated health benefits to offspring via glucan and/or a fucan supplementation of the maternal diet. Accordingly the present invention provides a composition comprising at least one glucan, at least one fucan, or at least one glucan and at least one fucan for use in improving or maintaining the gastrointestinal health or function of a progeny of a maternal animal by administration to the maternal animal, and a method for improving or maintaining the gastrointestinal health or function of a progeny of a maternal animal, the method comprising administering a composition comprising at least one glucan, at least one fucan, or at least one glucan and at least one fucan to the maternal animal.

41 Claims, 4 Drawing Sheets

(56) References Cited

OTHER PUBLICATIONS

MacFarlane et al. (1990) "Effect of Different Carbohydrates on Growth, Polysaccharidase and Glucosidase Production by *Bacteroides ovatus*, in Batch and Continuous Culture," J Appl Bact 68:179-187.

MacFarlane et al. (2003) "Regulation of Short-Chain Fatty Acid Production," Proc Nutr Soc 62:67-72.

Mackie et al. (1999) "Developmental Microbial Ecology of the Neonatal Gastrointestinal Tract," Amer J Clin Nutr 69(suppl):1035S-1045S.

O'Connell et al. (2005) "The Effect of Cereal Type and Exogenous Enzyme Supplementation in Pig Diets on Nutrient Digestibility, Intestinal Microflora, Volatile Fatty Acid Concentration and Manure Ammonia Emissions from Finisher Pigs," Animal Science 81:357-364.

O'Doherty et al. (2004) "The Interaction Between Lactofeed Level and Soya-Bean Meal on Growth Performance of Weanling Pigs," Animal Science 78:419-427.

O'Doherty et al. (2005) "Interaction Between Lactose Levels and Antimicrobial Growth Promoters on Growth Performance of Weanling Pigs," J Sci Food Agricult 85:371-380.

Partridge et al. (1993) "New Approaches with Pig Weaner Diets," In: Wiseman et al. (Eds), Recent Advances in Animal Nutrition, Nottingham University Press, U.K., pp. 221-248.

Pie et al. (2004) "Weaning is Associated with an Upregulation of Expression of Inflammatory Cytokines in the Intestine of Piglets," J Nutrition 134:641-647.

Pierce et al. (2005) "Performance of Weanling Pigs Offered Low or High Lactose Diets Supplemented with Avilamycin or Inulin," Anim Sci 80:313-318.

Pierce et al. (2006) "The Effect of Lactose and Inulin on Intestinal Morphology, Selected Microbial Populations and Volatile Fatty Acid Concentrations in the Gastro-Intestinal Tract of the Weanling Pig," Animal Science 82:311-318.

Pollmann et al. (1980) "Effect of *Lactobacillus acidophilus* on Starter Pigs Fed a Diet Supplemented with Lactose," J Anim Sci 51(3):638-644.

Read et al. (1996) "Analysis of the Structural Heterogeneity of Laminarin by Electrospray-Ionisation-Mass Spectrometry," Carbohydrate Research 281:187-201.

Reilly et al. (2008) "The Effects of Seaweed Extract Inclusion on Gut Morphology, Selected Intestinal Microbiota, Nutrient Digestibility, Volatile Fatty Acid Concentrations and the Immune Status of the Weaned Pig," Animal 2(10):1465-1473, published online Jul. 15, 2008.

Topping et al. (2001) "Short-Chain Fatty Acids and Human Colonic Function: Roles of Resistant Starch and Nonstarch Polysaccharides," Physiological Reviews 81(3):1031-1064.

* cited by examiner

Average percentage eosinophil of pigs fed different diets on day 14 post- inoculation Average terminal weight (Kg) of pigs weaned onto different diets and then challenged with PCV2 and PPV

OF GASTROINTESTINAL HEALTH, IMMUNITY AND PERFORMANCE BY DIETARY INTERVENTION

CROSS-REFERENCE TO RELATED APPLICATIONS

This application is a United States National Stage Application filed under 35 U.S.C. §371 of International Application No. PCT/EP2010/003088, filed May 21, 2010, which claims the benefit of Irish Application No. 2009/0398, filed May 21, 2009. Both of these applications are hereby incorporated by reference in their entireties.

FIELD OF THE INVENTION

The invention relates to the improvement of gastrointestinal health, immunity and performance by direct dietary intervention with laminarin and/or alpha-fucan and the transfer of associated health benefits to offspring via laminarin and/or alpha-fucan supplementation of the maternal diet.

In particular, the invention has the purpose of improving the nutritional, immunological and microbiological status of suckling and weaned offspring by supplementation of the maternal diet with laminarin and/or alpha-fucans. In another aspect, this invention relates to the utilisation of laminarin and/or alpha-fucan-containing preparations or feedstuffs to improve the immune status and immune response in pigs, poultry, sheep, horses, rabbits, fish, cats, dogs, humans and other monogastric subjects. Other aspects relate to the use of such compounds to increase performance in livestock as manifested by increased weight gain and feed conversion indices in weaned stock through maternal transfer of beneficial compounds in utero or via colostrum and breast milk during suckling, following supplementation of the maternal diet with laminarin and/or alpha-fucan.

In another aspect, the invention relates to manipulating the sterile conditions of the intestine of neonates by reducing total microbiological populations or by selectively encourage beneficial bacteria and inhibit growth of pathogens within the gastrointestinal system. Another aspect relates to the increasing the production of straight chain volatile fatty acids and reducing the production of branched chain volatile fatty acids within the gut by increasing fermentation from carbohydrate substrate and reducing fermentation from protein substrate. Yet another aspect relates to the synthesis of long chain polyunsaturated fatty acids including conjugated linoleic acid and omega-3 fatty acids by selectively stimulating *Bifidobacteria* in the intestinal tract.

In another aspect, the invention relates to the upregulation of mucin and/or trefoil factor (TFF) production in-vivo, thereby enhancing protection and stability of the gastrointestinal mucosa against insult, infection or injury.

BACKGROUND TO THE INVENTION

Paediatric clinicians and veterinarians are well-informed on the importance of achieving optimal nutrition during pregnancy to achieve successful physical, cognitive and neural development. Several trials have demonstrated the effects associated with deficiencies or toxicities of nutrients and other compounds on foetal development and its subsequent phenological characterisation. This has highlighted the importance of prenatal and perinatal dietary interventions to achieve optimal development during the critical stages and a healthy growth rate post partum.

To compound these issues, the publication of the Swann report (1969) encouraged a more stringent control of antibiotic usage in animal feeds due to the risks associated with antibiotic resistance, specifically the imposing threat on public health. This led to the EU prohibition of growth promoting antibiotics in animal feeds in January 2006. The prohibition of these growth promoters created a void in the market for intensive farming producers and also presented an opportunity for sourcing of a natural, safe alternative. The inclusion of laminarin and/or alpha-fucan in lactation diets of pigs, poultry, horses, sheep, rabbits, fish, humans and other monogastric subjects will have a major effect on the critical immunological and microbiological status at and immediately following parturition and will therefore have a major effect on consequent welfare, development and growth rates.

Algal beta-glucans, called laminarin, consist of beta $(1\rightarrow3)$-D glucosyl subunits with occasional $(1\rightarrow6)$ linked branches. Laminarin from *Laminaria digitata* occurs as two homologous series of molecules, a minor G series containing 22-28 glucosyl residues and a more abundant M series consisting of 20-30 glucosyl residues linked to a mannitol residue. Laminarin from many species of *Laminaria* (including *Laminaria hyperborea*) is relatively insoluble and consists of predominantly beta $(1\rightarrow3)$ chains while laminarin from *Laminaria digitata* is soluble and consists of small but significant levels of beta $(1\rightarrow6)$ linked branches. (Read et al, 1996).

Yeast beta glucans are found in long linear chains of up to 1300-1500 glucose residues linked by beta $(1\rightarrow3)$ bonds with a minor incidence of beta $(1\rightarrow6)$ chains. Laminarin has much smaller chain lengths (average=24 residues) with occasional beta $(1\rightarrow6)$ branches, depending on the species. *Laminaria digitata* has the beta $(1\rightarrow6)$ branching which make the glucans derived from them water soluble. Other *Laminaria* species, like *Laminaria hyperborea*, do not have this branching which makes the linear chains aggregate and makes the glucans derived from it, insoluble.

Natural polysaccharides built essentially of sulfated alpha-L-fucose residues are known as fucoidan (or alpha-fucans). These are present in brown algae, some echinoderms and are the second most predominant polysaccharide in brown seaweed, like *Ascophyllum nodosum* and species of *Laminaria*. alpha-Fucans have been extensively studied due to their diverse biological activities, since they are potent anticoagulant, antitumor, and antiviral agents.

The present invention encompasses the use of alpha-fucans, in particular the fucans present in sea plants, such as the sea cucumber body wall; in particular the alpha-fucan present in the cell walls of marine algae, and the egg jelly coat of sea urchin eggs. Ideally the present invention utilises fucoidan, the alpha-fucan present in macroalgae.

OBJECT OF THE INVENTION

It is an object of this invention to provide a novel method of controlling microbiological, immunological and performance related attributes of livestock such as pig, poultry, horse as well as rabbits, fish, cats, dogs and human neonates through maternal transfer mechanisms, by ensuring early delivery of beneficial compounds at critical growth stages. Another object is to provide prenatal dietary intervention with a laminarin and/or alpha-fucan containing preparation in the maternal diet for delivery through prenatal exchange in-utero or by postnatal transfer in colostrum or breastmilk. Another object is to provide a dosing regimen for laminarin and/or alpha-fucan containing preparations for controlling microbiological, immunological and performance related attributes of livestock such as pigs, poultry, horses, as well as rabbits, cats, dogs, fish and human.

It is a further object of the invention that the composition will beneficially affect the immune response by altering the expression of pro- and anti-inflammatory cytokines, leukocytes population and expression of immunoglobulins, mucins and trefoil factors.

Further objects of the invention include increasing the production of volatile straight chained fatty acids and reducing production of branched chain fatty acids (such as valeric, isovaleric and isobutyric acids) by altering the microbiological profile in favour of one that preferentially metabolises carbohydrates as fermentation substrate.

SUMMARY OF THE INVENTION

According to a first aspect of the present invention, there is provided a composition comprising at least one glucan, at least one fucan, or at least one glucan and at least one fucan for use in improving or maintaining the gastrointestinal health or function of a progeny of a maternal animal by administration to the maternal animal.

According to a second aspect of the present invention, there is provided a method for improving or maintaining the gastrointestinal health or function of a progeny of a maternal animal, the method comprising administering a composition comprising at least one glucan, at least one fucan, or at least one glucan and at least one fucan to the maternal animal.

The composition may comprise at least one glucan. When the composition comprises more than one glucan, each glucan may be the same glucan or a different glucan. Optionally or additionally, the composition may comprise at least one fucan. When the composition comprises more than one fucan, each fucan may be the same fucan or a different fucan. Optionally, the composition comprises at least on glucan, at least one fucan, or a mixture or combination thereof.

Optionally, the composition is administered to the maternal animal perinatally, prenatally, and/or postnatally. By "prenatally" is meant during the period of time extending from initiation (fertilisation) to approximately 50% of the total gestational term. Prenatal improvement or maintenance of the gastrointestinal health or function of the progeny can occur during prenatal administration. By "perinatally" is meant during the period of time extending from approximately 50% of the total gestational term to the time of birth. Perinatal improvement or maintenance of the gastrointestinal health or function of the progeny can occur during perinatal administration. By "postnatally" is meant during the period of time extending from the time of birth, and is intended to extend to the period post-weaning (the period following the time that the progeny ceases to ingest maternal colostrum or milk). Postnatal improvement or maintenance of the gastrointestinal health or function of the progeny can occur during postnatal administration.

By "progeny" is meant the offspring of a maternal animal, and is intended to include offspring developing in utero during the prenatal period, and offspring developing ex vivo during the postnatal period.

By "glucan" is meant a polysaccharide molecule comprising at least two saccharide monomers, optionally D-glucose monomers, wherein each monomer is linked to an adjacent monomer by a glycosidic bond. The polysaccharide molecule may be linear or branched i.e. the polysaccharide molecule can be a straight-chain polysaccharide or a branched chain polysaccharide. Optionally, the glucan is a branched chain glucan. The glucan may be an alpha glucan or a beta glucan. Optionally, the glucan is a beta glucan. By "beta glucan" is meant a glucan comprising at least one beta glycosidic bond. A glycosidic bond is intended to mean a glycosidic bond, wherein a carbon atom of a first monomer forms a bond, optionally a single order bond, with a carbon atom on an adjacent monomer. A beta glycosidic bond is intended to mean a glycosidic bond, wherein a functional group, optionally a hydroxyl group, attached to a carbon atom of a first monomer extends above the plane of the monomer (equatorially). Optionally, the C1 carbon atom of a first monomer forms a bond, optionally a single order bond, with the C6 carbon atom on an adjacent monomer. Further optionally, the glucan comprises a beta (1→6) glycosidic bond, optionally an oxygen-containing beta (1→6) glycosidic bond. Optionally, at least one glucan is beta (1→3, 1→6) glucan. Still further optionally, the glucan is laminarin.

By "fucan" is meant a polysaccharide, optionally a sulphated polysaccharide, comprising at least two fucose saccharide monomers, wherein each monomer is linked to an adjacent monomer by a glycosidic bond. The polysaccharide molecule may be linear or branched. Optionally, the fucan is a branched fucan. The fucan may be an alpha fucan or a beta fucan. Optionally, the fucan is an alpha fucan. By "alpha fucan" is meant a fucan comprising at least one alpha glycosidic bond. A glycosidic bond is intended to mean a glycosidic bond, wherein a carbon atom of a first monomer forms a bond, optionally a single order bond, with a carbon atom on an adjacent monomer. An alpha glycosidic bond is intended to mean a glycosidic bond, wherein a functional group, optionally a hydroxyl group, attached to a carbon atom of a first monomer extends below the plane of the monomer (axially). Optionally, the C1 carbon atom of a first monomer forms a bond, optionally a single order bond, with either the C3 or C4 carbon atom on an adjacent monomer. Optionally, the fucan is fucoidan. Optionally, the glucan and/or the fucan is isolated from a brown alga, optionally brown seaweed. Optionally, the brown alga is a brown macroalga. Optionally, the brown macroalga, optionally brown seaweed, is selected from Phaeophyceae, optionally selected from Phaeophyceae Laminariales and Phaeophyceae Fucales. Further optionally, the brown alga, optionally brown seaweed, is selected from Laminariaceae, Fucaceae, and Lessoniaceae. Optionally, the brown macroalga, optionally brown seaweed, is selected from *Ascophyllum* species, optionally *Ascophyllum nodosum* and *Laminaria* species, optionally *Laminaria digitata, Laminaria hyperborea, Laminaria saccharina, Laminaria japonica* or *Sargassum* species.

Alternatively, the glucan and/or the fucan is isolated from a red alga, optionally red seaweed. Optionally, the red alga is a red macroalga. Optionally, the red macroalga, optionally red seaweed, is selected from Florideophyceae, optionally selected from Florideophyceae Gigantinales, optionally selected from Gigartinaceae.

Optionally, the composition is administered daily to the maternal animal.

Optionally, the composition is administered, optionally daily, to the maternal animal in an amount such that about 3-50 milligrams of glucan per kilogram of body weight is administered to the maternal animal. Further optionally, the composition is administered, optionally daily, to the maternal animal in an amount such that about 2-40 milligrams of fucan per kilogram of body weight is administered to the maternal animal.

Optionally, the composition is administered, optionally daily, to the animal in an amount such that about 3-50 milligrams of glucan per kilogram of body weight is administered to the animal. Further optionally, the composition is administered, optionally daily, to the animal in an amount such that about 2-40 milligrams of fucan per kilogram of body weight is administered to the animal.

Optionally, the animal is a monogastric animal. Further optionally, the animal is selected from pigs, poultry, horses, sheep, rabbits, fish, cats, dogs, and humans.

By "improving or maintaining the gastrointestinal health or function" is meant improving the physiological function or histology of the gastrointestinal tract and/or the microbiological population of the gastrointestinal tract. Moreover, gastrointestinal health or function can be improved or maintained at the molecular level by improving the immunological state of the host. The improvement or maintenance of gastrointestinal health or function is intended to prevent or prophylactically treat disorders associated with poor gastrointestinal health or function, such as Crohn's disease, irritable bowel syndrome, and other such chronic conditions. Other disorders associated with poor gastrointestinal health are less serious and can include food-borne pathogens and certain bacteria and viruses that often result in diarrhoea, poor stool quality, low birth weight or weight gain, or other symptoms of poor gastrointestinal health.

Optionally, the gastrointestinal health or function is improved or maintained by increasing the concentration of immunoglobulin, optionally Immunoglobulin G, in the colostrum or milk of the maternal animal.

Optionally, the gastrointestinal health or function is improved or maintained by increasing the concentration of crude protein in the colostrum or milk of the maternal animal.

Optionally, the gastrointestinal health or function is improved or maintained by decreasing bacterial, optionally pathogenic bacterial, infection in the progeny. Further optionally, the bacterial, optionally pathogenic bacterial, infection is an Enterobacteriaceae infection, optionally selected from *Salmonella* and *Escherichia coli*.

Optionally, the gastrointestinal health or function is improved or maintained by increasing the expression of cytokines, optionally selected from tumour necrosis factor alpha, interleukin-1 alpha, interleukin-6, and trefoil factor 3.

Optionally, the gastrointestinal health or function is improved or maintained by decreasing the concentration of volatile branched-chain fatty acids, optionally selected from isobutyric acid, valeric acid, and isovaleric acid.

Optionally, the gastrointestinal health or function is improved or maintained by altering the concentration or activity of phagocytes, optionally leukocytes, neutrophils, eosinophils, monocytes, or lymphocytes, further optionally leukocytes, eosinophils or lymphocytes. Further optionally, the concentration or activity of leukocytes is increased and/or the concentration or activity of lymphocytes is decreased and/or the concentration or activity of eosinophils is decreased.

According to a further aspect of the present invention, there is provided a composition comprising at least one glucan, at least one fucan, or at least one glucan and at least one fucan for use in improving or maintaining the gastrointestinal health or function of an animal by administration to the animal in an amount such that about 3-50 milligrams of glucan per kilogram of body weight is administered, optionally daily, to the animal; or by administration to the animal in an amount such that about 2-40 milligrams of fucan per kilogram of body weight is administered, optionally daily, to the animal.

According to a still further aspect of the present invention, there is provided a method for improving or maintaining the gastrointestinal health or function of an animal, the method comprising administering a composition comprising at least one glucan, at least one fucan, or at least one fucan and at least one fucan to the animal in an amount such that about 3-50 milligrams of glucan per kilogram of body weight is administered, optionally daily, to the animal; or by administration to the animal in an amount such that about 2-40 milligrams of fucan per kilogram of body weight is administered, optionally daily, to the animal.

Optionally, the composition further comprises a sugar, optionally a disaccharide, optionally selected from lactose, sucrose, lactulose, and maltose. Further optionally, the composition further comprises sugar, optionally a disaccharide, optionally selected from lactose, sucrose, lactulose, and maltose.

Optionally, the gastrointestinal health or function is improved or maintained by decreasing bacterial infection, optionally *Escherichia coli* infection.

Optionally, the gastrointestinal health or function is improved or maintained and prevents or prophylactically treats diarrhoea.

Optionally, the gastrointestinal health or function is improved or maintained by increasing the expression of cytokines, optionally in the presence of antigen. Further optionally, the antigen is bacterial antigen, optionally bacterial lipopolysaccharide. Optionally, the cytokine is selected from interleukin-6 and interleukin-8.

Optionally, the gastrointestinal health or function is improved or maintained by increasing the expression of mucins, optionally mucin-2 and/or mucin-4.

Optionally, the gastrointestinal health or function is improved or maintained by decreasing the concentration of circovirus or parvovirus, optionally porcine circovirus or porcine parvovirus. Further optionally, the porcine circovirus is type-2 porcine circovirus.

Optionally, the gastrointestinal health or function is improved or maintained by increasing the concentration of straight-chain volatile fatty acids.

The inventors have developed a composition consisting of a formulation of laminarin and/or alpha-fucans that has altering effects on: (I) gut histology, (II) gut microbiology, (III) pro- and anti-inflammatory cytokine expression, (III) neonatal serum immunoglobulin levels, (IV) mucin production, (V) trefoil factor production, (VI) nutritional and immunological composition of colostrum and breast milk and (VII) performance indices. In addition, there were clear detrimental effect on intestinal *Enterobacteria* populations which has associated benefits in reduced morbidity and mortality rates from reduced infection and inflammation.

Accordingly, the present invention provides use of a composition comprising beta-glucans and/or alpha-fucans in a method of improving neonatal and weanling gastrointestinal health and immunity through pre- and postnatal supplementation of the maternal diet. In preferred embodiments, beta-glucans and alpha-fucans may be derived from more than one source including seaweed and some echinoderms. The seaweed may be from the group consisting of Laminariaceae, Fucacea, Gigartinaceae or Lessoniaceae.

The invention also provides use of a composition comprising beta-glucans and/or alpha-fucans:

in a method of producing a maternal dietary supplement or feedstuff, for reducing gastrointestinal bacterial populations in neonates and weanlings;

in a method of producing a maternal dietary supplement or feedstuff, for reducing morbidity and mortality rates in neonates and weanlings;

in a method of producing a maternal dietary supplement or feedstuff, for improving digestive histology by increasing the villus height, reducing the crypt depth or increasing the overall villus height:crypt depth ratio in neonates and weanlings;

in a method of producing a maternal dietary supplement or feedstuff, for improving performance in the progeny of livestock such as pigs, poultry, horses, as well as rabbits, fish, cats, dogs and humans including an increase in average daily gain, an increase in average daily feed intake and an improvement in feed efficiency;

in a method of improving gastrointestinal health by encouraging beneficial microflora, reducing pathogenic microflora and improving performance in neonates and weanlings, by supplementing maternal diets in a method of upregulating the production of mucins and trefoil factors by epithelial cells as a means of enhanced physical protection of the gastrointestinal epithelium.

In a further aspect the invention provides methods of achieving the above-mentioned effects by feeding a composition comprising beta-glucans and/or alpha-fucans to humans, non-human animals or poultry.

In a still further aspect, the invention provides:

a dosing regimen for preventing bacterial or viral infection and inflammation in livestock such as pigs, poultry, horses, sheep as well as rabbits, fish, cats, dogs and humans by directly supplementing the diet or by supplementing the maternal diet in pre- and postnatal periods with a composition comprising beta-glucans and alpha-fucans;

a dosing regimen for improving the nutritional quality and increasing the immunoglobulin levels of colostrum and breast milk by supplementing the maternal diet in the pre- and postnatal periods with a composition comprising beta-glucans and/or alpha-fucans;

a dosing regimen for increasing neonatal serum immunoglobulin levels by in-utero transfer of beneficial immunostimulatory compounds across the placental membrane by supplementing the maternal diet in the pre- and postnatal periods with a composition comprising beta glucans and/or alpha fucans;

a dosing regimen for increasing neonatal serum immunoglobulin levels through an increased uptake in colostrum or breast milk by supplementing the maternal diet in the pre- and postnatal periods with a composition comprising beta glucans and/or alpha fucans;

a dosing regimen for reducing *Enterobacteria*, including *E. coli*, populations in the digestive tracts of neonatal pigs, poultry, horses, as well as rabbits, fish, cats, dogs, humans and other monogastric subjects by supplementing the maternal diet in the pre- and postnatal periods with a composition comprising beta glucans and/or alpha fucans;

a dosing regimen for alleviating functional intestinal disorders associated with weaning by supplementing the maternal diet in the pre- and postnatal periods with a composition comprising beta glucans and/or alpha fucans;

a dosing regimen for encouraging a healthy intestinal microbiological profile in neonates and weanlings by selectively encouraging a dominant ratio of beneficial bacteria and selectively inhibiting the growth of pathogenic bacteria in the period of bacterial colonisation of intestine immediately after birth by supplementing the maternal diet in the pre- and postnatal periods with a composition comprising beta glucans and/or alpha fucans.

The dosing regimen for administration of laminarin may be a daily dosage administered at greater than 3 milligrams of laminarin per kilogram of body weight per day to a maximum of 50 milligrams per kilogram of body weight per day.

The dosing regimen for administration of alpha fucans may be a daily dosage administered of greater than 2 milligrams per kilogram of body weight per day to a maximum of 40 milligrams per kilogram of body weight per day.

The dosing regimen for administration of a combination of laminarin and alpha fucans may be a daily dosage of laminarin administered greater than 3 milligrams per kilogram of body weight per day to a maximum of 50 milligrams per kilogram of body weight per day in combination with a daily dosage of alpha-fucans greater than 2 milligrams per kilogram of body weight per day to a maximum of 50 milligrams per kilogram of body weight per day.

The invention also provides use of a composition comprising beta-glucans and/or alpha-fucans in a method:

for increasing straight chain volatile fatty acid production in-vivo;

for reducing branched chain volatile fatty acid production in-vivo and their excretion;

for increasing long chain polyunsaturated fatty acids production in-vivo;

for improving immune status and response in immune-challenged livestock such as pigs, poultry, horses, as well as rabbits, fish, humans and other monogastric subjects.

for improving the immune status by increased expression of pro- and anti-inflammatory cytokines, mucins and trefoil factors.

BRIEF DESCRIPTION OF THE DRAWINGS

Embodiments of the present invention will now be described by the use of non-limiting examples, and reference made to the accompanying drawings, in which.

EXAMPLES

Figure 1:
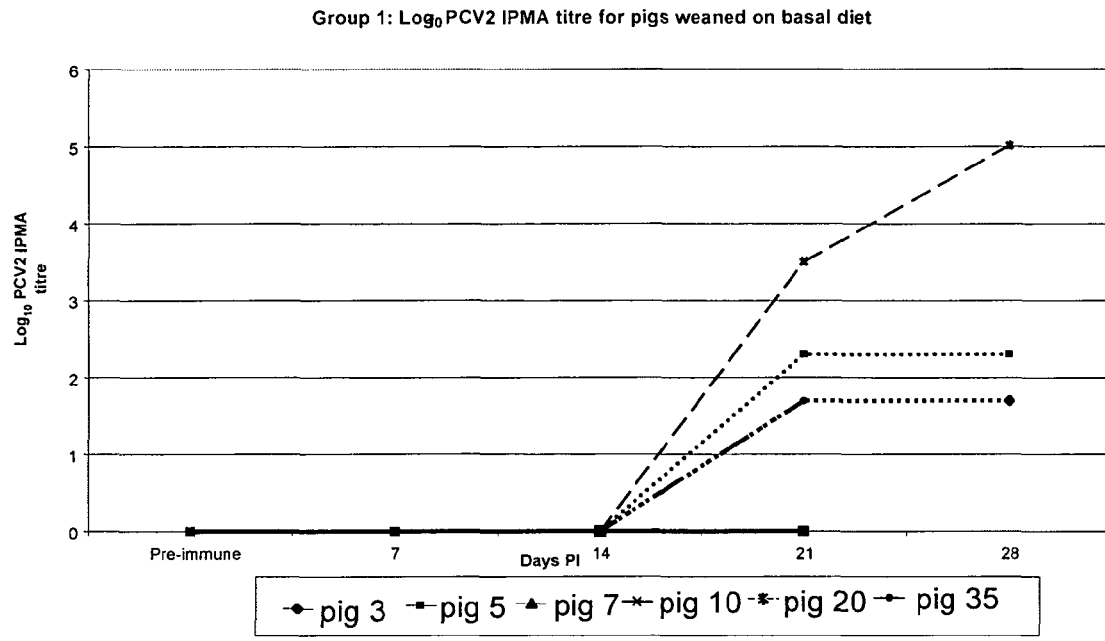
FIG. 1 illustrates PCV2-specific antibody titres of piglets fed a basal diet.

The examples given are results of investigative research on the effects of laminarin and/or fucoidan supplementation on porcine subjects as a model for all monogastrics including humans, animals and poultry. The examples shown include trials carried out using seaweed extract containing laminarin and fucoidan in combination (hereafter referred to as SWE) or each of the compounds individually as laminarin (hereafter referred to as LAM) or fucoidan (hereafter referred to as FUC).

Example 1

Materials and Methods

Animals and Treatment 40 pregnant sows were assigned to 1 of 4 dietary treatments (n=10 sows/treatment): (T1) basal lactation; (T2) basal lactation+100 g/day fish oil (F.O.); (T3) basal lactation+1.8 g/day SWE; and (T4) basal lactation+100 g/day F.O.+1.8 g/day SWE from day 109 of gestation until weaning at 26 days. SWE contained daily doses of laminarin (1 g) and fucoidan (0.8 g). For the test subjects, diets were top-dressed daily with the experimental supplement. At birth, weight was recorded and 3 piglets were selected to represent the mean birth weight of the litter. These were weighed weekly until weaning. At weaning, 120 mixed sex pigs (3 pigs per litter; average weight=8.05±0.46 Kg) were selected and offered starter diets for 21 days. Feed and water were available ad libitum throughout the experiment. Pigs were individually weighed on the day of weaning (day 0) and thereafter at 7, 14 and 21 days post weaning. Feed intake recorded on a daily basis.

Sample Collection 30 ml of colostrum and milk was collected from sows on days 0 and 12 post farrowing. Blood samples were collected from the jugular veins of 2 piglets/litter on day 5 and 12 of lactation for immunoglobulin analysis. Crude protein was determined in accordance with the Association of Official Analytical Chemists (AOAC, 1995).

Quantification of Immunoglobulins

Immunoglobulin assays were performed using specific pig ELISA quantification kits (Bethyl Laboratories, Inc., Montgomery, Tex., USA). Porcine assays were performed on sow colostrum and milk and piglet serum as described by Ilsley and Miller (2005).

Analysis of Selected Microbial Populations

Digesta samples were aseptically removed from the caecum and colon of each pig post-slaughter. Populations of *Bifidobacterium, E. coli* and *Lactobacillus* spp. were selectively isolated and enumerated according to Pierce et al. (2006).

Volatile Fatty Acid (VFA) Analysis

Samples of digesta from the caecum and colon were recovered for VFA analysis by a gas chromatographic method following the procedures of Pierce et al. (2006).

Histological Analysis

Sections of duodenum, jejunum and ileum were aseptically removed, excised and fixed in 10% phosphate-buffered formalin. Cross sections at 5 μm thickness of each intestinal segment were stained with haemotoxylin and eosin. Villus height and crypt depth were measured using a light microscope fitted with an image analyser (Image Pro Plus; Media Cybernetics, Bethesda, Md. USA).

Phagocytosis Estimation of Blood Cells by Flow Cytometry

The PHAGOTEST® kit (Orpegen Pharma, Heidelberg, Germany), measuring the uptake of unopsonised, FITC-labelled *E. coli*, was used to measure the phagocytosing activity in whole blood cells. Samples were analyzed using a Dako Cyan-ADP flow cytometer (Dako, Glostrup, Denmark).

Ileum and Colon Gene Expression—RNA Extraction and cDNA Synthesis

Tissue samples were collected from the ileum and colon, rinsed with ice-cold PBS and immediately placed into tubes containing RNAlater® (Ambion Inc, Austin, Tex.). Total RNA was extracted using a Gene Elute Mammalian Total RNA Miniprep Kit (Sigma-Aldrich) and quantified using a NanoDrop-ND1000 Spectrophotometer (Thermo Fisher Scientific Inc. MA, USA). Purity was assessed by determining the absorbance ratio at 260 and 280 nm. Total RNA was reverse transcribed (RT) utilising a First Strand cDNA Synthesis Kit (Fermentas) using oligo dT primers.

Quantitative Real-Time PCR (qPCR)

Quantitative real-time PCR (qPCR) assays were performed on cDNA samples on a 7900HT ABI Prism Sequence Detection System (PE Applied Biosystems, Foster City, Calif.) using SYBR Green PCR Master Mix (Applied Biosystems). All primers used for RT-PCR (IL-1α, IL-6, IL-10, TNF-α, MUC2, TFF3, GAPDH, B2M, ACTB, PPIA and YWHAZ) were designed using Primer Express™ software. Amplification was carried out in 10 μl SYBR PCR Mastermix, 1 μl forward and reverse primer, 8 μl DPEC treated water and 1 μl of template cDNA. Dissociation analyses of the PCR product was performed to confirm the specificity of the resulting PCR products.

Results

Colostrum and Milk Composition

Colostral IgG levels were significantly higher in SWE supplemented sows (p<0.01). Supplementation increased protein concentration in sow's milk on day 12 (p<0.05).

TABLE 1

Effect of dietary treatment on total solid, crude protein, crude fat and immunoglobulin concentrations of sow colostrum and milk

| | | | | | | | p-value | | |
|---|---|---|---|---|---|---|---|---|---|
| FO | 0 g/day | | 100 g/day | | | | | SWE × | |
| SWE - 1.8 g/day | No | Yes | No | Yes | SEM | SWE | FO | FO |
| Colostrum | | | | | | | | |
| Total solids % | 24.78 | 25.20 | 25.69 | 24.89 | 1.422 | 0.897 | 0.834 | 0.673 |
| Crude protein % | 13.27 | 13.90 | 14.72 | 14.31 | 1.145 | 0.925 | 0.423 | 0.656 |
| Fat % | 6.27 | 6.10 | 5.93 | 5.04 | 0.737 | 0.478 | 0.352 | 0.632 |
| IgG (mg/ml) | 62.52 | 70.11 | 64.01 | 69.56 | 2.557 | 0.010 | 0.844 | 0.681 |
| IgA (mg/ml) | 10.30 | 8.93 | 10.50 | 8.69 | 1.022 | 0.105 | 0.980 | 0.819 |
| IgM (mg/ml) | 4.08 | 4.91 | 3.86 | 4.11 | 0.444 | 0.238 | 0.263 | 0.513 |
| Sows milk | | | | | | | | |
| Total solids % | 20.11 | 20.22 | 19.48 | 19.77 | 0.486 | 0.687 | 0.273 | 0.851 |
| Crude protein % | 5.17 | 5.42 | 5.17 | 5.36 | 0.109 | 0.050 | 0.837 | 0.761 |
| Fat % | 9.02 | 8.80 | 8.51 | 8.36 | 0.546 | 0.731 | 0.388 | 0.940 |
| IgG (mg/ml) | 0.37 | 0.44 | 0.45 | 0.49 | 0.056 | 0.297 | 0.204 | 0.772 |
| IgA (mg/ml) | 3.59 | 3.72 | 4.03 | 3.83 | 0.331 | 0.914 | 0.370 | 0.584 |
| IgM (mg/ml) | 1.56 | 1.56 | 2.10 | 1.56 | 0.419 | 0.519 | 0.514 | 0.526 |

Suckling Piglet Immunoglobulins

Piglets suckling SWE supplemented sows had significantly higher serum IgG concentrations on day 5 ($p<0.01$) and day 12 of lactation ($p<0.05$) and enhanced serum IgA concentrations on day 5 of lactation ($p>0.05$).

TABLE 2

Serum immunoglobulin concentrations in piglets suckling supplemented sows.

| FO | | | | | | | p-value | | |
|---|---|---|---|---|---|---|---|---|---|
| SWE - | 0 g/day | | 100 g/day | | | | | SWE × |
| 1.8 g/day | No | Yes | No | Yes | SEM | SWE | FO | FO |
| Immunoglobulins (mg/ml) | | | | | | | | |
| Day 5 | | | | | | | | |
| IgG | 17.63 | 23.02 | 20.98 | 22.80 | 1.253 | 0.006 | 0.213 | 0.160 |
| IgA | 3.00 | 3.24 | 2.02 | 3.02 | 0.278 | 0.033 | 0.036 | 0.174 |
| IgM | 1.52 | 1.61 | 1.41 | 1.39 | 0.222 | 0.881 | 0.468 | 0.805 |

TABLE 2-continued

Serum immunoglobulin concentrations in piglets suckling supplemented sows.

| FO | | | | | | | p-value | | |
|---|---|---|---|---|---|---|---|---|---|
| SWE - | 0 g/day | | 100 g/day | | | | | SWE × |
| 1.8 g/day | No | Yes | No | Yes | SEM | SWE | FO | FO |
| Day 12 | | | | | | | | |
| IgG | 9.91 | 12.47 | 10.07 | 11.62 | 0.880 | 0.025 | 0.689 | 0.570 |
| IgA | 0.35 | 0.27 | 0.41 | 0.39 | 0.090 | 0.598 | 0.324 | 0.776 |
| IgM | 0.53 | 0.61 | 0.54 | 0.63 | 0.051 | 0.098 | 0.789 | 0.929 |

Suckling Piglet Performance

Piglets suckling SWE supplemented sows had significantly lower average daily gains ($p<0.05$) during week 1 of lactation. There were no significant differences in daily gains between birth and weaning. Litter size, litter weight, piglet birth weight and weaning weight were not influenced by sow dietary treatments.

TABLE 3

Effect of maternal SWE supplementation on litter size, litter weight, piglet live weight and average daily gain (ADG)

| +FO | 0 | | 100 | | | p-value | | |
|---|---|---|---|---|---|---|---|---|
| +SWE 1.8 g/day | No | Yes | No | Yes | SEM | SWE | FO | SWE × FO |
| Litter size, n | 12.40 | 12.40 | 12.40 | 12.35 | 0.710 | 0.968 | 0.958 | 0.968 |
| Litter weight (Kg) | 14.59 | 15.80 | 16.04 | 14.7 | 0.958 | 0.924 | 0.861 | 0.154 |
| Birth weight (Kg) | 1.25 | 1.28 | 1.28 | 1.27 | 0.061 | 0.828 | 0.921 | 0.656 |
| Piglet BW (Kg) | | | | | | | | |
| Day 7 | 3.37 | 2.92 | 3.20 | 2.91 | 0.161 | 0.016 | 0.546 | 0.612 |
| Day 14 | 5.41 | 4.73 | 5.16 | 4.80 | 0.233 | 0.021 | 0.697 | 0.462 |
| Day 21 | 7.31 | 6.58 | 6.67 | 6.52 | 0.280 | 0.093 | 0.185 | 0.274 |
| Day 26 | 8.73 | 7.85 | 7.85 | 7.76 | 0.340 | 0.127 | 0.131 | 0.209 |
| ADG (Kg/day) | | | | | | | | |
| Day 0 to 7 | 0.230 | 0.195 | 0.236 | 0.216 | 0.014 | 0.045 | 0.319 | 0.589 |
| Day 8 to 15 | 0.282 | 0.263 | 0.274 | 0.259 | 0.013 | 0.185 | 0.635 | 0.804 |
| Day 15 to 21 | 0.286 | 0.277 | 0.237 | 0.260 | 0.018 | 0.674 | 0.053 | 0.353 |
| Day 21 to 26 | 0.264 | 0.254 | 0.240 | 0.266 | 0.022 | 0.694 | 0.779 | 0.384 |
| Day 0 to 26 | 0.277 | 0.256 | 0.250 | 0.254 | 0.012 | 0.501 | 0.236 | 0.294 |

Post-Weaning Piglet Performance

Piglets from SWE supplemented sows had significantly higher ADG from day 7-14 ($p<0.05$) and day 0-21 ($p=0.063$) and feed intake ($p<0.05$) between days 7-14 post weaning.

TABLE 4

Effect of maternal dietary supplementation with SWE and FO from day 109 of gestation until weaning (day 26) on post-weaning performance.

| | SWE | | | FO | | | p-value | |
|---|---|---|---|---|---|---|---|---|
| Treatment | No | Yes | SEM | No | Yes | SEM | SWE | FO |
| ADG (Kg/day) | | | | | | | | |
| Day 0 to 7 | 0.091 | 0.104 | 0.018 | 0.089 | 0.106 | 0.018 | 0.634 | 0.518 |
| Day 7 to 14 | 0.282 | 0.335 | 0.017 | 0.278 | 0.340 | 0.017 | 0.042 | 0.016 |
| Day 14 to 21 | 0.450 | 0.476 | 0.019 | 0.485 | 0.441 | 0.017 | 0.351 | 0.115 |
| Day 0 to 21 | 0.275 | 0.308 | 0.012 | 0.284 | 0.299 | 0.012 | 0.063 | 0.403 |
| ADFI (Kg/day) | | | | | | | | |
| Day 0 to 7 | 0.169 | 0.174 | 0.013 | 0.167 | 0.175 | 0.013 | 0.781 | 0.691 |
| Day 7 to14 | 0.366 | 0.424 | 0.017 | 0.394 | 0.396 | 0.017 | 0.025 | 0.932 |

TABLE 4-continued

Effect of maternal dietary supplementation with SWE and FO from day 109 of gestation until weaning (day 26) on post-weaning performance.

| Treatment | SWE | | | FO | | | p-value | |
|---|---|---|---|---|---|---|---|---|
| | No | Yes | SEM | No | Yes | SEM | SWE | FO |
| Day 14 to 21 | 0.669 | 0.669 | 0.050 | 0.655 | 0.713 | 0.050 | 0.669 | 0.417 |
| Day 0 to 21 | 0.401 | 0.433 | 0.019 | 0.405 | 0.428 | 0.019 | 0.186 | 0.288 |
| Gain:feed ratio | | | | | | | | |
| Day 0 to 7 | 0.444 | 0.532 | 0.080 | 0.456 | 0.519 | 0.080 | 0.439 | 0583 |
| Day 7 to 14 | 0.764 | 0.779 | 0.030 | 0.699 | 0.844 | 0.030 | 0.719 | 0.002 |
| Day 14 to 21 | 0.692 | 0.741 | 0.032 | 0.755 | 0.678 | 0.032 | 0.289 | 0.107 |
| Day 0 to 21 | 0.634 | 0.692 | 0.030 | 0.639 | 0.686 | 0.030 | 0.258 | 0.407 |

Microbiology

In the colon, maternal SWE supplementation resulted in a significant decrease in *Bifidobacteria* populations ($p<0.01$). Furthermore, SWE supplementation had a tendency to decrease *E. coli* and *Lactobacillus* populations in the colon compared to the control ($p=0.09$).

TABLE 5

Effect of maternal dietary supplementation with SWE and FO from day 109 of gestation until weaning on selected intestinal microflora in the 9 day old weaned pig.

| FO (g/day) | 0 | | 100 | | | p-value | | |
|---|---|---|---|---|---|---|---|---|
| SWE (1.8 g/day) | No | Yes | No | Yes | SEM | SWE | FO | SWE × FO |
| Caecum ($Log_{10}$ CFU/g digesta) | | | | | | | | |
| *Bifidobacteria* spp. | 8.52 | 8.57 | 8.54 | 8.30 | 0.211 | 0.652 | 0.563 | 0.506 |
| *Lactobacilli* spp. | 8.15 | 8.14 | 8.41 | 7.93 | 0.328 | 0.466 | 0.926 | 0.486 |
| *E. coli* | 4.89 | 3.67 | 3.37 | 3.78 | 0.387 | 0.311 | 0.081 | 0.048 |
| Colon ($Log_{10}$ CFU/g digesta) | | | | | | | | |
| *Bifidobacteria* spp. | 8.91 | 8.53 | 9.32 | 8.11 | 0.276 | 0.008 | 0.998 | 0.148 |
| *Lactobacilli* spp. | 8.50 | 8.33 | 8.99 | 8.01 | 0.322 | 0.087 | 0.775 | 0.222 |
| *E. coli* | 5.51 | 4.62 | 5.16 | 4.38 | 0.473 | 0.093 | 0.535 | 0.917 |

Cytokine Gene Expression

In the ileum of the post weaned pig, maternal SWE supplementation induced a significant increase in the expression of the pro-inflammatory cytokine TNF-α ($p<0.01$). A significant increase in TFF 3 gene expression was also observed in the colon ($p<0.05$).

TABLE 6

Effect of maternal dietary supplementation with SWE from day 109 of gestation until weaning on selected gene expression in the ileum and colon of the weaned pig.

| Treatment | SWE | | | FO | | | p-value | |
|---|---|---|---|---|---|---|---|---|
| | No | Yes | SEM | No | Yes | SEM | SWE | FO |
| Ileum | | | | | | | | |
| IL-1α | 0.216 | 0.215 | 0.034 | 0.224 | 0.206 | 0.034 | 0.984 | 0.741 |
| IL-6 | 0.212 | 0.166 | 0.032 | 0.197 | 0.181 | 0.032 | 0.325 | 0.747 |
| TNF-α | 0.164 | 0.575 | 0.102 | 0.264 | 0.475 | 0.106 | 0.010 | 0.182 |
| IL-10 | 0.127 | 0.075 | 0.023 | 0.085 | 0.116 | 0.023 | 0.122 | 0.371 |
| MUC 2 | 0.518 | 0.724 | 0.132 | 0.635 | 0.608 | 0.132 | 0.281 | 0.859 |
| TFF 3 | 0.585 | 0.708 | 0.076 | 0.664 | 0.629 | 0.076 | 0.266 | 0.766 |
| Colon | | | | | | | | |
| IL-1α | 0.150 | 0.132 | 0.025 | 0.099 | 0.182 | 0.025 | 0.632 | 0.029 |
| IL-6 | 0.170 | 0.124 | 0.026 | 0.102 | 0.193 | 0.102 | 0.236 | 0.024 |
| TNF-α | 0.242 | 0.206 | 0.026 | 0.214 | 0.234 | 0.026 | 0.338 | 0.592 |
| IL-10 | 0.132 | 0.077 | 0.022 | 0.089 | 0.121 | 0.022 | 0.092 | 0.324 |
| MUC 2 | 0.490 | 0.508 | 0.095 | 0.616 | 0.381 | 0.095 | 0.733 | 0.182 |
| TFF 3 | 0.371 | 0.565 | 0.068 | 0.536 | 0.400 | 0.068 | 0.045 | 0.111 |

Volatile Fatty Acid (VFA) Analysis and pH Measurement

TABLE 7

Effect of maternal dietary treatment with SWE and FO from day 109 of gestation until weaning on VFA composition of intestinal contents of the 9 day old weaned pig.

| FO (g/day) | 0 | | 100 | | | p-value | | |
|---|---|---|---|---|---|---|---|---|
| SWE (1.8 g/day) | No | Yes | No | Yes | SEM | SWE | FO | SWE × FO |
| Caecum (mmol/g digesta) | | | | | | | | |
| Total VFA | 181.7 | 168.0 | 170.4 | 183.2 | 11.20 | 0.968 | 0.865 | 0.249 |
| Acetic acid | 0.660 | 0.645 | 0.675 | 0.665 | 0.011 | 0.289 | 0.124 | 0.801 |
| Propionic acid | 0.228 | 0.245 | 0.240 | 0.245 | 0.010 | 0.298 | 0.539 | 0.542 |
| Butyric acid | 0.093 | 0.089 | 0.063 | 0.074 | 0.008 | 0.664 | 0.009 | 0.371 |
| Isobutyric acid | 0.003 | 0.003 | 0.004 | 0.002 | 0.001 | 0.308 | 0.949 | 0.295 |
| Valeric acid | 0.011 | 0.012 | 0.012 | 0.010 | 0.002 | 0.823 | 0.686 | 0.492 |
| Isovaleric acid | 0.005 | 0.006 | 0.006 | 0.004 | 0.001 | 0.582 | 0.572 | 0.264 |
| Acetic:propionic acid | 2.94 | 2.68 | 2.84 | 2.75 | 0.158 | 0.287 | 0.897 | 0.624 |
| BCFAs* | 0.020 | 0.021 | 0.022 | 0.016 | 0.003 | 0.482 | 0.623 | 0.226 |
| pH | 6.17 | 6.27 | 6.41 | 6.07 | 0.189 | 0.511 | 0.922 | 0.255 |
| Colon (mmol/g digesta) | | | | | | | | |
| Total VFA | 151.6 | 146.0 | 128.1 | 168.7 | 12.62 | 0.177 | 0.974 | 0.080 |
| Acetic acid | 0.658 | 0.631 | 0.672 | 0.663 | 0.014 | 0.209 | 0.113 | 0.521 |
| Propionic acid | 0.216 | 0.229 | 0.281 | 0.232 | 0.356 | 0.617 | 0.344 | 0.386 |
| Butyric acid | 0.087 | 0.010 | 0.087 | 0.077 | 0.012 | 0.799 | 0.268 | 0.269 |
| Isobutyric acid | 0.007 | 0.008 | 0.012 | 0.006 | 0.002 | 0.080 | 0.317 | 0.043 |
| Valeric acid | 0.011 | 0.016 | 0.019 | 0.012 | 0.002 | 0.705 | 0.471 | 0.038 |
| Isovaleric acid | 0.012 | 0.013 | 0.021 | 0.010 | 0.002 | 0.053 | 0.222 | 0.028 |
| Acetic:propionic acid | 3.07 | 2.79 | 3.18 | 2.95 | 0.184 | 0.166 | 0.462 | 0.883 |
| BCFAs* | 0.030 | 0.036 | 0.052 | 0.028 | 0.005 | 0.127 | 0.195 | 0.009 |
| pH | 6.28 | 6.17 | 6.48 | 6.44 | 0.119 | 0.554 | 0.063 | 0.783 |

*BCFAs, branched chain fatty acids

Histology

In the ileum, there was a significant effect of SWE supplementation on villus height and villus height to crypt depth ratio ($p<0.05$). Results from the duodenum also showed a beneficial effect emulating from SWE supplementation on crypt depth ($p>0.10$)

TABLE 8

Effect of maternal dietary supplementation with SWE and fish oil (FO) from day 109 of gestation until weaning (day 26) on villus height, crypt depth and villus height to crypt depth ratio in the 9 day old weaned pig.

| Fish oil (g/d) | 0 | | 100 | | | p-value | | |
|---|---|---|---|---|---|---|---|---|
| SWE (1.8 g/d) | No | Yes | No | Yes | SEM | SWE | FO | SWE × FO |
| Villous height (μm) | | | | | | | | |
| Duodenum | 419.4 | 415.9 | 430.1 | 421.5 | 5.62 | 0.291 | 0.183 | 0.645 |
| Jejunum | 384.2 | 396.2 | 395.4 | 382.8 | 5.00 | 0.952 | 0.843 | 0.022 |
| Ileum | 215.0 | 233.0 | 238.7 | 232.6 | 6.00 | 0.328 | 0.063 | 0.055 |
| Crypt depth (μm) | | | | | | | | |
| Duodenum | 328.8 | 314.3 | 316.0 | 315.4 | 4.40 | 0.097 | 0.216 | 0.122 |
| Jejunum | 288.6 | 280.3 | 291.7 | 288.1 | 6.87 | 0.392 | 0.458 | 0.731 |
| Ileum | 178.0 | 172.4 | 167.9 | 171.7 | 4.75 | 0.853 | 0.270 | 0.333 |
| Villous:crypt depth ratio | | | | | | | | |
| Duodenum | 1.28 | 1.31 | 1.36 | 1.32 | 0.02 | 0.788 | 0.049 | 0.164 |
| Jejunum | 1.33 | 1.43 | 1.36 | 1.33 | 0.03 | 0.288 | 0.177 | 0.034 |
| Ileum | 1.21 | 1.36 | 1.42 | 1.35 | 0.04 | 0.444 | 0.015 | 0.013 |

Phagocytosing Capacity

SWE supplementation exerted a suppressive effect on total eosinophil numbers (p<0.01) in suckling piglets. Dietary SWE supplementation resulted in a higher percentage of *E. coli* phagocytosing leukocytes (p<0.05) and a lower percentage of *E. coli* phagocytosing lymphocytes (p<0.01) compared to non SWE-supplemented diets.

TABLE 9

Effect of dietary treatment on the phagocytosing activity (total number and % positive phagocytosis) of piglet whole blood cells at weaning

|  | SWE | | | FO | | | p-value | |
| --- | --- | --- | --- | --- | --- | --- | --- | --- |
|  | No | Yes | SEM | No | Yes | SEM | SWE | FO |
| Leukocytes | 22475 | 20912 | 6637 | 20896 | 22492 | 1637 | 0.595 | 0.365 |
| Positive % | 57.6 | 64 | 2.2 | 57.1 | 64.5 | 2.2 | 0.046 | 0.024 |
| Lymphocytes | 6650 | 5127 | 672 | 6292 | 5485 | 672 | 0.116 | 0.575 |
| Positive % | 13.3 | 10.1 | 0.834 | 10.5 | 12.9 | 0.834 | 0.008 | 0.050 |
| Monocytes | 2641 | 2578 | 83 | 2575 | 2644 | 83 | 0.627 | 0.614 |
| Positive % | 74.1 | 77.7 | 2.8 | 72.7 | 79.1 | 2.8 | 0.369 | 0.112 |
| Neutrophils | 8650 | 9489 | 883 | 7977 | 10161 | 883 | 0.407 | 0.076 |
| Positive % | 91.1 | 92.1 | 1.2 | 91.4 | 91.9 | 1.2 | 0.564 | 0.796 |
| Eosinophils | 512 | 338 | 61 | 384 | 466 | 61 | 0.002 | 0.297 |
| Positive % | 26 | 21.8 | 2.1 | 23.2 | 24.6 | 2.1 | 0.163 | 0.653 |

Example 2

Experiment 1

Materials and Methods

Experimental Design and Diets

Experiment 1 was designed as a complete randomised design comprising of five dietary treatments as follows: (T1) 0 g/Kg SWE (control), (T2) 0.7 g/Kg SWE, (T3) 1.4 g/Kg SWE extract, (T4) 2.8 g/Kg SWE extract and (T5) 5.6 g/Kg SWE extract. The SWE contained LAM+FUC. All diets were formulated to have identical concentrations of net energy and total lysine. The amino acid requirements were met relative to lysine (Close, 1994). Chromic oxide was added at the time of milling to all diets at the rate of 150 ppm for the determination of ash digestibility.

Animals and Management 30 finishing boars with an initial live weight of 51±3.4 Kg were used in the experiment. The pigs were blocked on the basis of live weight and randomly allocated to one of five dietary treatments. The pigs were allowed a 14-day dietary adaptation period after which time they were weighed and transferred to individual metabolism crates. Animals were allowed a 5-day acclimatisation period, followed by a 5-day collection period to facilitate an apparent digestibility and nitrogen balance study. The daily feed allowance (DE intake=3.44×(live weight)$^{0.54}$ (Close, 1994) was divided over two meals. Water was provided with meals in a 1:1 ratio. Between meals, fresh water was provided ad libitum. The metabolism crates were located in an environmentally controlled room, maintained at a constant temperature of 22° C. (±1.5° C.).

Coefficient of Total Tract Apparent Digestibility (CTTAD) and Nitrogen Balance Study During collections, urine was collected in a plastic container, via a funnel below the crate, containing 20 ml of sulphuric acid (25% $H_2SO_4$). To avoid nitrogen volatilisation, the funnel was sprayed four times daily with weak sulphuric acid (2% $H_2SO_4$) solution. The urine volume was recorded daily and a 50 ml sample was collected and frozen for laboratory analysis. Total faeces weight was recorded daily and oven dried at 100° C. A sample of freshly voided faeces was collected daily and frozen for nitrogen analysis and pH measurement. At the end of the collection period, the faeces samples were pooled and a sub-sample retained for laboratory analysis. Feed samples were collected each day and retained for chemical analysis. All 30 pigs remained on their respective dietary treatments until slaughter.

Example 2

Experiment 2

Materials and Methods

Experimental Design and Diets

This experiment was designed as a 2×2 factorial design comprising four dietary treatments: (T1) control diet, (T2) control+300 ppm LAM, (T3) control+238 ppm FUC, (T4) control+300 ppm LAM+238 ppm FUC. All diets were standardised for net energy (9.8 MJ/Kg) and total lysine (10 g/Kg). Amino acid requirements were met relative to lysine (Close, 1994).

TABLE 10

Composition and analysis of diets - experiment 1 (as fed basis).

|  | Treatment | | | | |
| --- | --- | --- | --- | --- | --- |
|  | 1 | 2 | 3 | 4 | 5 |
| Ingredients (g · kg$^{-1}$) | | | | | |
| *Laminaria hyperborea* extract | 0 | 0.7 | 1.4 | 2.8 | 5.6 |
| Wheat | 704.3 | 703.6 | 702.9 | 701.5 | 698.7 |
| Soybean Meal | 265 | 265 | 265 | 265 | 265 |
| Soya Oil | 5.7 | 5.7 | 5.7 | 5.7 | 5.7 |
| Mineral and Vitamin† | 2.5 | 2.5 | 2.5 | 2.5 | 2.5 |
| Limestone | 15 | 15 | 15 | 15 | 15 |
| Dicalcium phosphate | 7.5 | 7.5 | 7.5 | 7.5 | 7.5 |
| Analysed Composition (g · kg$^{-1}$) | | | | | |
| Laminarin | 0 | 0.075 | 0.150 | 0.300 | 0.600 |
| Fucoidan | 0 | 0.059 | 0.119 | 0.238 | 0.476 |
| Dry Matter | 869.1 | 871.8 | 886.5 | 884.4 | 878.2 |
| Crude Protein (N × 6.25) | 215.7 | 203.2 | 199.5 | 200.8 | 195.1 |
| Neutral Detergent Fibre | 119.7 | 97.8 | 91.8 | 96.4 | 98 |

TABLE 10-continued

Composition and analysis of diets - experiment 1 (as fed basis).

| | Treatment | | | | |
|---|---|---|---|---|---|
| | 1 | 2 | 3 | 4 | 5 |
| Acid detergent fibre | 39.0 | 35.2 | 30.7 | 32.7 | 35.7 |
| Crude Ash | 45.7 | 48.4 | 47.7 | 51.2 | 52.6 |
| Lysine | 9.9 | 9.9 | 9.9 | 9.9 | 9.9 |
| Methionine and cysteine$ | 6.0 | 6.0 | 6.0 | 6.0 | 6.0 |
| Threonine | 7.0 | 7.0 | 7.0 | 7.0 | 7.0 |
| Tryptophan | 1.9 | 1.9 | 1.9 | 1.9 | 1.9 |
| Calculated composition (g · kg$^{-1}$) | | | | | |
| Digestible Energy# | 13.9 | 13.9 | 13.9 | 13.9 | 13.8 |
| Calcium | 7.29 | 7.29 | 7.30 | 7.32 | 7.35 |
| Phosphorus | 4.04 | 4.04 | 4.04 | 4.04 | 4.04 |

†Provided per kg of complete diet: 3 mg retinol, 0.05 mg cholecalciferol, 40 mg alpha-tocopherol, 90 mg copper as copper II sulphate, 100 mg iron as iron II sulphate, 100 mg zinc as zinc oxide, 0.3 mg selenium as sodium selenite, 25 mg manganese as manganous oxide and 0.2 mg iodine as calcium iodate on a calcium sulphate/calcium carbonate carrier.

Animals and Management 28 finishing boars with an initial live weight of 55 Kg were used. Pigs were blocked on the basis of live weight and were randomly allocated to one of four dietary treatments. The pigs were allowed a 28-day dietary adaptation period after which time they were weighed and slaughtered.

Microbiology and Apparent Digestibility of Ash in the Proximate Caecum and Colon Digesta was aseptically removed from the proximal caecum and colon of each animal after slaughter. Chromic oxide was used as marker to determine ash digestibility in the caecum and colon. *Bifidobacteria* spp., *Lactobacillus* spp. and *Enterobacteria* were isolated and counted according to the method described by O'Connell et al., (2005).

Volatile Fatty Acid Sampling and Analysis

Samples of digesta from the caecum and the proximal and distal colon of individual pigs were taken for VFA analysis. VFA concentrations in the digesta were determined using a modified method of Porter and Murray (2001) according to O'Connell et al. (2005).

Results

Experiment 1—Microbiology Study

TABLE 11

Effect of SWE concentration on microbial ecology and pH in the caecum and colon

| | Treatment | | | | | | | |
|---|---|---|---|---|---|---|---|---|
| L. hyperborea extract (g/Kg) | 1<br>0 | 2<br>0.7 | 3<br>1.4 | 4<br>2.8 | 5<br>5.6 | s.e.m. | Linear | Quadratic |
| Proximal Caecum Bacterial Populations (CFU/ml digesta) | | | | | | | | |
| Enterobacteria spp. | 6.94 | 7.15 | 6.65 | 6.42 | 6.70 | 0.196 | ns | * |
| Bifidobacteria spp. | 8.33 | 8.45 | 8.41 | 8.25 | 7.86 | 0.174 | ** | ns |
| Lactobacilli spp. | 8.67 | 8.85 | 8.73 | 8.84 | 8.62 | 0.140 | ns | ns |
| Proximal Colon Bacterial Populations (CFU/ml digesta) | | | | | | | | |
| Enterobacteria | 6.95 | 6.72 | 6.34 | 6.49 | 6.85 | 0.245 | ns | * |
| Bifidobacteria spp. | 8.37 | 8.62 | 8.77 | 8.57 | 8.16 | 0.118 | ns | ** |
| Lactobacilli spp. | 9.10 | 9.15 | 9.07 | 8.90 | 8.83 | 0.113 | * | ns |
| Caecum pH | 5.63 | 5.90 | 6.42 | 5.49 | 5.69 | 0.125 | ns | *** |
| Colon pH | 5.94 | 6.11 | 6.18 | 5.85 | 5.94 | 0.079 | ns | ** |

* = ($p < 0.05$),
** = ($p < 0.01$),
*** = ($p < 0.001$),
ns = non significant ($p > 0.05$),
$ = ($p < 0.1$)

Experiment 1—CFAsc: Total Lysine (10.0 Analysis Segmentation Substrate. Thereof the Gastrointestinal Surfacetion thereof to Increase the Production Apparent Ash Digestibility

TABLE 12

Effect of SWE concentration on apparent nutrient digestibility and nitrogen balance.

| | Treatment | | | | | | | |
|---|---|---|---|---|---|---|---|---|
| L. hyperborea SWE | 1<br>0 | 2<br>0.7 | 3<br>1.4 | 4<br>2.8 | 5<br>5.6 | s.e.m. | Linear | Quadratic |
| Average Daily Feed Intake (g/d) | 2158 | 2168 | 2138 | 2214 | 2209 | | * | |
| Laminarin Intake (mg/d) | 0 | 162.6 | 320.7 | 664.2 | 1325.4 | | | |
| Fucoidan Intake (mg/d) | 0 | 127.9 | 254.4 | 526.9 | 1051.4 | | | |
| Water Intake (Kg/d) | 5.11 | 4.65 | 5.44 | 5.80 | 6.08 | 0.043 | * | ns |
| Urine Output (Kg/day) | 2.803 | 3.256 | 3.654 | 3.445 | 4.273 | 0.320 | * | ns |
| Nitrogen Intake (g/day) | 64.72 | 61.48 | 60.48 | 62.90 | 60.51 | 0.691 | * | ns |

TABLE 12-continued

Effect of SWE concentration on apparent nutrient digestibility and nitrogen balance.

| | Treatment | | | | | | | |
|---|---|---|---|---|---|---|---|---|
| | 1 | 2 | 3 | 4 | 5 | | | |
| L. hyperborea SWE | 0 | 0.7 | 1.4 | 2.8 | 5.6 | s.e.m. | Linear | Quadratic |
| | Digestibility Coefficients | | | | | | | |
| Neutral Detergent Fibre | 0.66 | 0.55 | 0.56 | 0.58 | 0.56 | 0.012 | ns | * |
| Nitrogen | 0.90 | 0.90 | 0.89 | 0.90 | 0.89 | 0.006 | ns | ns |
| Dry Matter | 0.89 | 0.89 | 0.89 | 0.89 | 0.89 | 0.002 | ns | ns |
| Organic Matter | 0.91 | 0.91 | 0.91 | 0.91 | 0.91 | 0.003 | ns | ns |
| | Ash Digestibility Coefficients | | | | | | | |
| Caecal Ash | 0.49 | 0.45 | 0.40 | 0.35 | 0.43 | 0.037 | ns | ** |
| Colonic Ash | 0.56 | 0.49 | 0.51 | 0.50 | 0.51 | 0.016 | ns | ** |
| Total Tract Ash | 0.57 | 0.62 | 0.56 | 0.62 | 0.62 | 0.010 | ** | ns |
| | Nitrogen (N) Balance | | | | | | | |
| Faecal N Excretion (g/day) | 6.93 | 6.93 | 7.02 | 7.34 | 7.16 | 0.417 | ns | ns |
| Urinary N Excretion (g/day) | 29.18 | 28.91 | 29.61 | 28.79 | 34.27 | 1.07 | ns | * |
| Total N Excretion (g/day) | 36.14 | 35.89 | 36.84 | 35.69 | 41.60 | 1.12 | ns | * |
| N Retention (g/day) | 25.87 | 26.12 | 25.18 | 26.31 | 20.41 | 1.17 | ns | * |

\* = ($p < 0.05$),
\*\* = ($p < 0.01$),
\*\*\* = ($p < 0.001$),
ns = non significant ($p > 0.05$)

Experiment 1—Volatile Fatty Acid Study

TABLE 13

Effect of SWE concentration on concentration & molar proportions of VFAs

| | Treatment | | | | | | | |
|---|---|---|---|---|---|---|---|---|
| | 1 | 2 | 3 | 4 | 5 | | | |
| L. hyperborea SWE | 0 | 0.7 | 1.4 | 2.8 | 5.6 | s.e.m. | Linear | Quadratic |
| | Proximal Caecum (mmol/L) | | | | | | | |
| VFAs | 281.2 | 241.7 | 378.1 | 197.9 | 227.8 | 13.91 | * | ** |
| Acetic acid | 0.626 | 0.656 | 0.653 | 0.621 | 0.629 | 0.011 | ns | ** |
| Propionic acid | 0.210 | 0.197 | 0.172 | 0.202 | 0.195 | 0.008 | ns | ** |
| Isobutyric acid | 0.014 | 0.011 | 0.017 | 0.014 | 0.005 | 0.002 | * | * |
| Butyric acid | 0.107 | 0.101 | 0.111 | 0.105 | 0.118 | 0.005 | ns | ns |
| Isovaleric acid | 0.020 | 0.017 | 0.023 | 0.027 | 0.014 | 0.002 | ns | ** |
| Valeric acid | 0.019 | 0.016 | 0.021 | 0.019 | 0.014 | 0.002 | ns | ns |
| Acetic:Propionic | 2.86 | 3.22 | 3.83 | 3.16 | 3.35 | 0.155 | ns | *** |
| BCFAs | 0.052 | 0.044 | 0.062 | 0.060 | 0.034 | 0.006 | ns | * |
| | Proximal Colon (mmol/L) | | | | | | | |
| VFAs | 342.3 | 376.8 | 371.7 | 281.0 | 369.0 | 45.31 | ns | ns |
| Acetic acid | 0.579 | 0.575 | 0.569 | 0.574 | 0.579 | 0.013 | ns | ns |
| Propionic acid | 0.201 | 0.196 | 0.200 | 0.206 | 0.195 | 0.004 | ns | ns |
| Isobutyric acid | 0.023 | 0.027 | 0.025 | 0.025 | 0.026 | 0.005 | ns | ns |
| Butyric acid | 0.123 | 0.132 | 0.133 | 0.130 | 0.126 | 0.006 | ns | ns |
| Isovaleric acid | 0.034 | 0.038 | 0.038 | 0.034 | 0.039 | 0.003 | ns | ns |
| Valeric acid | 0.030 | 0.035 | 0.033 | 0.028 | 0.033 | 0.005 | ns | ns |
| Acetic:Propionic | 2.801 | 3.032 | 2.839 | 2.784 | 2.869 | 0.099 | ns | ns |
| BCFAs | 0.088 | 0.101 | 0.097 | 0.088 | 0.099 | 0.016 | ns | ns |

\* = ($p < 0.05$),
\*\* = ($p < 0.01$),
\*\*\* = ($p < 0.001$),
ns = non significant ($p > 0.05$)

Experiment 2—Microbiology Study

TABLE 14

Effect of LAM and FUC on the concentration and molar proportions of VFAs

| | Treatment | | | | | Significance | | |
|---|---|---|---|---|---|---|---|---|
| | 1 | 2 | 3 | 4 | | | | |
| | Control | LAM | FUC | LAM/FUC | s.e.m. | LAM | FUC | LAM × FUC |
| Proximal Colon (mmol/L) | | | | | | | | |
| Total VFA | 168.7 | 173.6 | 195.5 | 197.9 | 7.925 | ns | ** | ns |
| Acetic acid | 0.618 | 0.576 | 0.599 | 0.647 | 0.011 | ns | * | *** |
| Propionic acid | 0.213 | 0.268 | 0.251 | 0.217 | 0.011 | ns | ns | *** |
| Isobutyric acid | 0.009 | 0.003 | 0.004 | 0.003 | 0.001 | ** | * | * |
| Butyric acid | 0.124 | 0.125 | 0.118 | 0.114 | 0.004 | ns | ns | ns |
| Isovaleric acid | 0.017 | 0.011 | 0.011 | 0.008 | 0.002 | * | * | ns |
| Valeric acid | 0.017 | 0.017 | 0.014 | 0.011 | 0.002 | ns | ** | ns |
| Acetic:propionic | 2.94 | 2.17 | 2.44 | 3.02 | 0.159 | ns | ns | *** |
| BCFAs | 0.042 | 0.031 | 0.026 | 0.022 | 0.004 | * | ** | ns |
| Distal Colon (mmol/L) | | | | | | | | |
| Total VFA | 126.02 | 136.7 | 172.6 | 159.5 | 9.34 | ns | *** | ns |
| Acetic acid | 0.597 | 0.571 | 0.599 | 0.636 | 0.012 | ns | ** | ** |
| Propionic acid | 0.195 | 0.203 | 0.186 | 0.181 | 0.005 | ns | *** | ns |
| Isobutyric acid | 0.026 | 0.022 | 0.021 | 0.020 | 0.001 | ns | ** | ns |
| Butyric acid | 0.118 | 0.134 | 0.139 | 0.113 | 0.007 | ns | ns | ** |
| Isovaleric acid | 0.040 | 0.034 | 0.034 | 0.032 | 0.002 | * | * | ns |
| Valeric acid | 0.024 | 0.023 | 0.021 | 0.018 | 0.001 | ns | *** | ns |
| Acetic:propionic | 3.08 | 2.76 | 3.23 | 3.52 | 0.128 | ns | *** | * |
| BCFAs | 0.089 | 0.078 | 0.076 | 0.070 | 0.003 | * | ** | ns |

Experiment 2—Volatile Fatty Acid Study

TABLE 15

Effect of LAM and FUC concentration on concentration and molar proportions of VFAs

| | Treatment | | | | | Significance | | |
|---|---|---|---|---|---|---|---|---|
| | 1 | 2 | 3 | 4 | | | | |
| | Control | LAM | FUC | LAM/FUC | s.e.m. | LAM | FUC | LAM × FUC |
| Proximal Colon (mmol/L) | | | | | | | | |
| Total VFA | 168.7 | 173.6 | 195.5 | 197.9 | 7.925 | ns | ** | ns |
| Acetic acid | 0.618 | 0.576 | 0.599 | 0.647 | 0.011 | ns | * | *** |
| Propionic acid | 0.213 | 0.268 | 0.251 | 0.217 | 0.011 | ns | ns | *** |
| Isobutyric acid | 0.009 | 0.003 | 0.004 | 0.003 | 0.001 | ** | * | * |
| Butyric acid | 0.124 | 0.125 | 0.118 | 0.114 | 0.004 | ns | ns | ns |
| Isovaleric acid | 0.017 | 0.011 | 0.011 | 0.008 | 0.002 | * | * | ns |
| Valeric acid | 0.017 | 0.017 | 0.014 | 0.011 | 0.002 | ns | ** | ns |
| Acetic:Propionic | 2.94 | 2.17 | 2.44 | 3.02 | 0.159 | ns | ns | *** |
| BCFAs | 0.042 | 0.031 | 0.026 | 0.022 | 0.004 | * | ** | ns |
| Distal Colon (mmol/L) | | | | | | | | |
| Total VFA | 126.02 | 136.7 | 172.6 | 159.5 | 9.34 | ns | *** | ns |
| Acetic acid | 0.597 | 0.571 | 0.599 | 0.636 | 0.012 | ns | ** | ** |
| Propionic acid | 0.195 | 0.203 | 0.186 | 0.181 | 0.005 | ns | *** | ns |
| Isobutyric acid | 0.026 | 0.022 | 0.021 | 0.020 | 0.001 | ns | ** | ns |
| Butyric acid | 0.118 | 0.134 | 0.139 | 0.113 | 0.007 | ns | ns | ** |
| Isovaleric acid | 0.040 | 0.034 | 0.034 | 0.032 | 0.002 | * | * | ns |
| Valeric acid | 0.024 | 0.023 | 0.021 | 0.018 | 0.001 | ns | *** | ns |
| Acetic:Propionic ratio | 3.08 | 2.76 | 3.23 | 3.52 | 0.128 | ns | *** | * |
| BCFAs | 0.089 | 0.078 | 0.076 | 0.070 | 0.003 | * | ** | ns |

\* = ($p < 0.05$),
\*\* = ($p < 0.01$),
\*\*\* = ($p < 0.001$),
ns = non significant ($p > 0.05$)

Example 3

Experimental Design and Diets

This experiment was carried out over two consecutive periods of 25 days. 240 piglets were selected after weaning at 24 days and assigned to one of four dietary treatments. Pigs in period 1 and 2 had initial live weights of 7.2 Kg and 7.8 Kg (±0.9 Kg), respectively. This experiment was designed as a 2×2 factorial. During the experiment (days 0-25) piglets were offered the following diets: (T1) 150 g/Kg lactose; (T2) 150 g/Kg lactose+SWE; (T3) 250 g/Kg lactose (T4) 250 g/Kg lactose+SWE. SWE was included at 2.8 g/Kg and derived from *Laminaria digitata*. It contained laminarin (112 g/Kg), fucoidan (89 g/Kg) and ash (799 g/Kg).

Animals and Management

Pigs were housed in groups of 4 (n=15/treatment) and weighed at weaning (day 0), day 7, 14 and 25. Pigs were fed ad libitum. Fresh faecal samples were collected on days 10 to 15 for determination of nutrient digestibility and VFA analysis. Fresh faecal samples were collected on day 10 for enumeration of *E. coli* and *Lactobacilli* (O'Connell et al., 2005).

Microbiology 1 g of faecal sample was serially diluted in maximum recovery diluent (MRD; Oxoid, Basingstoke, UK) and plated on selective agars. *Lactobacillus* spp. were isolated on de Man Rogosa Sharp agar (MRS, Oxoid). The API 50 CHL (BioMerieux, France) kit was used to confirm suspect *Lactobacilli* spp. *E. coli* species were isolated on MacConkey agar (Oxoid). Suspect colonies were confirmed with API 20E (BioMerieux, France).

Results

Performance

TABLE 16

The effect of lactose and SWE on piglet performance

| | Treatment | | | | | Significance | | |
|---|---|---|---|---|---|---|---|---|
| | 1 | 2 | 3 | 4 | SEM | Lactose | SWE | Lactose × SWE |
| Lactose (g/Kg) | 150 | | 250 | | | | | |
| SWE | − | + | − | + | | | | |
| Average Daily Gain (ADG) (Kg/day) | | | | | | | | |
| Day 0-7 | 0.100 | 0.148 | 0.146 | 0.183 | 0.018 | * | * | ns |
| Day 7-14 | 0.302 | 0.303 | 0.325 | 0.387 | 0.021 | * | ns | ns |
| Day 14-25 | 0.438 | 0.427 | 0.388 | 0.455 | 0.020 | ns | ns | * |
| Day 0-25 | 0.275 | 0.293 | 0.287 | 0.350 | 0.013 | * | ** | ns |

TABLE 16-continued

The effect of lactose and SWE on piglet performance

| | Treatment | | | | | Significance | | |
|---|---|---|---|---|---|---|---|---|
| | 1 | 2 | 3 | 4 | SEM | Lactose | SWE | Lactose × SWE |
| Average Daily Feed Intake (ADFI) (Kg/day) | | | | | | | | |
| Day 0-7 | 0.242 | 0.257 | 0.239 | 0.271 | 0.015 | ns | ns | ns |
| Day 7-14 | 0.415 | 0.426 | 0.450 | 0.472 | 0.019 | * | ns | ns |
| Day 14-25 | 0.682 | 0.663 | 0.683 | 0.737 | 0.025 | ns | ns | ns |
| Day 0-25 | 0.446 | 0.449 | 0.458 | 0.502 | 0.014 | * | ns | ns |
| Gain: Feed ratio (Kg/Kg) | | | | | | | | |
| Day 0-7 | 0.413 | 0.558 | 0.589 | 0.659 | 0.062 | * | ns | ns |
| Day 7-14 | 0.747 | 0.705 | 0.729 | 0.832 | 0.055 | ns | ns | ns |
| Day 14-25 | 0.633 | 0.636 | 0.569 | 0.622 | 0.027 | * | ns | ns |
| Day 0-25 | 0.603 | 0.633 | 0.619 | 0.691 | 0.062 | ns | * | ns |

Probability of significance;
* $P < 0.05$;
** $P < 0.01$,
ns $P > 0.05$

Coefficient of Total Tract Apparent Digestibility (CTTAD)

TABLE 17

The effect of dietary treatment on the coefficient of total tract apparent digestibility

| | Treatment | | | | | Significance | | |
|---|---|---|---|---|---|---|---|---|
| | 1 | 2 | 3 | 4 | SEM | Lactose | SWE | Lactose × SWE |
| Lactose (g/Kg) | 150 | | 250 | | | | | |
| SWE | − | + | − | + | | | | |
| Digestibility (%) | | | | | | | | |
| DM | 87.75 | 91.65 | 91.34 | 95.25 | 0.500 | *** | *** | ns |
| OM | 89.16 | 92.52 | 92.24 | 95.82 | 0.535 | *** | *** | ns |
| N | 83.69 | 89.59 | 86.86 | 92.34 | 1.038 | * | *** | ns |
| Ash | 53.30 | 70.60 | 72.80 | 83.08 | 2.140 | *** | *** | ns |
| GE | 85.93 | 90.93 | 90.22 | 94.46 | 0.698 | *** | *** | ns |
| NDF | 37.55 | 65.01 | 61.91 | 74.60 | 2.970 | *** | *** | * |

Probability of significance;
* $p < 0.05$;
** $p < 0.01$,
*** $p < 0.001$,
ns $p > 0.05$

Microbiology and VFAs

TABLE 18

Effect of dietary treatment on Lactobacilli and *Escherichia coli* populations

| | Treatment | | | | | Significance | | |
|---|---|---|---|---|---|---|---|---|
| | 1 | 2 | 3 | 4 | SEM | Lactose | SWE | Lactose × SWE |
| Lactose (g/Kg) | 150 | | 250 | | | | | |
| SWE | − | + | − | + | | | | |
| Bacterial populations ($Log_{10}$ CFU/g faeces) | | | | | | | | |
| Lactobacilli | 8.46 | 8.63 | 8.19 | 8.84 | 0.12 | ns | *** | * |
| *Escherichia coli* | 6.30 | 5.80 | 5.70 | 4.50 | 0.42 | * | * | ns |

Probability of significance;
* $P < 0.05$;
** $P < 0.01$,
ns $P > 0.05$

Example 4

Experimental Design and Diets

One hundred and ninety two piglets were weaned at twenty four days of age, with an initial live weight of 6.4±0.785 Kg and assigned to one of four dietary treatments or 21 days post weaning. The dietary treatments consisted of (T1) basal diet, (T2) basal diet with 300 ppm LAM, (T3) basal diet with 236 ppm FUC, (T4) Basal diet with 300 ppm LAM and 236 ppm FUC. Diets were formulated to have identical concentrations of digestible energy (DE) (16 MJ/Kg) and ileal digestible lysine (14 g/Kg). All amino acid requirements were met relative to lysine (Close, 1994). Chromium III oxide was added to the diets for determination of nutrient digestibility. The LAM and FUC were derived from *Laminaria hyperborea.*

Management

Piglets were housed in groups of 4 and offered feed twice daily. Water was supplied ad-libitum. Any pig displaying symptoms of illness was treated appropriately and recorded. Pigs were weighed on day 0 (day of weaning), 7, 14 and 21. Feed intake was monitored weekly. Fresh faecal samples were taken on day 10 and were analysed for *E. coli* and *Lactobacilli* concentrations. Faeces samples were collected from each pen on day 12-17 and were retained for chemical analysis. Fresh faecal samples were removed on day 14 and were frozen and retained for volatile fatty acid analysis. Fresh faecal samples were taken on day 17 for pH determination.

Faeces Scoring and Morbidity

Pigs were observed for clinical signs of diarrhoea from day 0-21. A scoring system was applied to indicate its presence and severity. The following scoring system was used: 1=hard, 2=slightly soft, 3=soft, partially formed, 4=loose, semi-liquid and 5=watery, mucous-like.

Microbiology

A sample was serially diluted (1:10) in 9.0 ml aliquots of maximum recovery diluent (MRD, Oxoid, Basingstoke, UK), and spread plated (0.1 ml aliquots) onto selective agars. *Lactobacillus* spp. were isolated on de Man, Rogosa, Sharp agar (MRS, Oxoid) with overnight incubation at 37° C. in 5% $CO_2$. The API 50 CHL (BioMerieux, France) kit was used to confirm suspect *Lactobacilli* spp. *E. coli* species were isolated on MacConkey agar (Oxoid), following aerobic incubation at 37° C. for 18-24 hours. Suspect colonies were confirmed with API 20E (BioMerieux, France).

Results

Performance

Pigs fed LAM supplemented diets had an increased ADG (0.344 v 0.266, p<0.01) during days 7-14 and during the entire experimental period (0.324 v 0.232, p<0.01) compared to pigs offered diets with no LAM. Pig fed LAM supplementation had improved gain:feed ratio during days 7-14 (0.763 vs. 0.569, p<0.001) and during the entire experimental period (0.703 v 0.646, p<0.05) compared to unsupplemented LAM diets. There was a significant interaction (p<0.05) between LAM and FUC supplementation on ADG during days 14-21. Pigs offered the FUC diet had a significantly higher ADG than pigs offered the basal diet, however there was no effect of FUC when added to a LAM diet. There was no effect of LAM or FUC inclusion on average daily feed intake.

TABLE 19

The effect of seaweed extract on pig performance post weaning.

| | Treatment | | | | | Significance | | |
| --- | --- | --- | --- | --- | --- | --- | --- | --- |
| | T1 | T2 | T3 | T4 | SEM | LAM | FUC | LAM × FUC |
| LAM | − | + | − | + | | | | |
| FUC | − | − | + | + | | | | |
| No of pens | 12 | 12 | 12 | 12 | | | | |
| Daily Gain (g/day) | | | | | | | | |
| D 0-7 | 181 | 178 | 166 | 185 | 0.025 | ns | ns | ns |
| D 7-14 | 268 | 320 | 265 | 368 | 0.022 | ** | ns | ns |
| D 14-21 | 418 | 459 | 475 | 430 | 0.016 | ns | ns | * |
| D 0-21 | 288 | 319 | 302 | 328 | 0.012 | * | ns | ns |
| Food Intake (g/day) | | | | | | | | |
| D 0-7 | 256 | 263 | 253 | 257 | 0.020 | ns | ns | ns |
| D 7-14 | 449 | 464 | 477 | 457 | 0.027 | ns | ns | ns |
| D 14-21 | 604 | 686 | 673 | 619 | 0.024 | ns | ns | ns |
| D 0-21 | 436 | 471 | 467 | 444 | 0.017 | ns | ns | ns |
| Gain to feed ratio (Kg/Kg) | | | | | | | | |
| D 0-7 | 0.666 | 0.646 | 0.646 | 0.679 | 0.055 | ns | ns | ns |
| D 7-14 | 0.579 | 0.707 | 0.561 | 0.818 | 0.049 | *** | ns | ns |
| D 14-21 | 0.716 | 0.673 | 0.708 | 0.697 | 0.039 | ns | ns | ns |
| Days 0-21 | 0.654 | 0.675 | 0.638 | 0.732 | 0.024 | * | ns | ns |

Probability of significance;
* = (P < 0.05),
** = (P < 0.01),
*** = (P < 0.001).

Faecal pH, DM, Faecal Score

Pigs offered diets supplemented with LAM had an increased faecal DM content (28.64 v 26.24; p<0.05) compared to unsupplemented LAM diets. Pigs offered diets supplemented with LAM had a decreased faecal score during days 7-14 (2.05 v 2.57; p<0.05). There was a significant interaction between LAM and FUC inclusion on faecal score during the entire experimental period (days 0-21) (P<0.05). Pigs offered the combination of LAM and FUC had a reduced faecal score compared to pigs offered the FUC alone diet. However, there was no effect of LAM inclusion on faecal score compared to the basal diet.

TABLE 20

Effect of dietary treatment on faecal dry matter and faecal score

|  | Treatment | | | | | Significance | | |
| --- | --- | --- | --- | --- | --- | --- | --- | --- |
|  | T1 | T2 | T3 | T4 | SEM | LAM | FUC | LAM × FUC |
| LAM | − | + | − | + | | | | |
| FUC | − | − | + | + | | | | |
| No of pens | 12 | 12 | 12 | 12 | | | | |
| Faecal DM (g/Kg) | 272.8 | 290.1 | 252.2 | 282.8 | 10.2 | * | ns | ns |
| Faecal pH | 6.42 | 6.25 | 6.19 | 6.31 | 0.109 | ns | ns | ns |
| Faecal score | | | | | | | | |
| Days 0-7 | 2.45 | 2.61 | 2.49 | 2.07 | 0.149 | ns | ns | ns |
| Days 7-14 | 2.62 | 2.22 | 2.53 | 1.88 | 0.196 | * | ns | ns |
| Days 14-21 | 1.58 | 1.93 | 1.77 | 1.62 | 0.119 | ns | ns | ns |
| Days 0-21 | 2.22 | 2.25 | 2.26 | 1.85 | 0.110 | ns | ns | * |

Probability of significance;
* = (P < 0.05)

Microbiology and Volatile Fatty Acids (VFAs)

Pigs offered LAM diets had a reduced faecal *E. coli* population compared to pigs offered diets with no LAM supplementation (7.22 vs. 7.84; p<0.05). There was a significant interaction (P<0.01) between LAM and FUC on faecal *Lactobacilli* populations. Pigs offered the FUC diet had increased *Lactobacilli* numbers compared to pigs offered the basal diet (9.22 v 8.93) however there was no effect of FUC on faecal *lactobacilli* populations when included with LAM. There was no significant effect of treatment on volatile fatty acid concentrations.

status and reduced coliform load in the gut of the pig. Modulation of mucosal immunity by the binding of LAM to the specific receptors of immune cells may provide beneficial effects on pig health through preventing the colonization and proliferation of bacteria and therefore the subsequent damage of the intestinal wall. The proliferation of *Lactobacilli* spp. in FUC supplemented diets would suggest that a proportion of the supplemented FUC is escaping hydrolysis in the foregut and passing into the colon for bacterial fermentation. Saccharolytic species of bacteria such as *Lactobacilli* spp. take part in the breakdown of complex carbohydrates. FUC is soluble

TABLE 21

The effect of dietary treatment on faecal Lactobacilli and *Escherichia coli* populations and faecal molar proportions of volatile fatty acids

|  | Treatment | | | | | Significance | | |
| --- | --- | --- | --- | --- | --- | --- | --- | --- |
|  | T1 | T2 | T3 | T4 | s.e.m | LAM | FUC | LAM × FUC |
| LAM | − | + | − | + | | | | |
| FUC | − | − | + | + | | | | |
| E. coli | 8.04 | 7.41 | 7.67 | 7.05 | 0.217 | * | ns | ns |
| Lactobacilli | 8.93 | 9.18 | 9.22 | 9.06 | 0.076 | ns | ns | ** |
| Total VFA (mmol/L) | | | | | | | | |
| Molar Proportions | 141.4 | 134.5 | 130.1 | 110.4 | 9.197 | ns | ns | ns |
| Acetic Acid | 0.568 | 0.568 | 0.590 | 0.588 | 0.014 | ns | ns | ns |
| Propionic Acid | 0.210 | 0.209 | 0.288 | 0.219 | 0.007 | ns | ns | ns |
| Isobutyric acid | 0.018 | 0.021 | 0.018 | 0.022 | 0.001 | ns | ns | ns |
| Butyric Acid | 0.144 | 0.135 | 0.152 | 0.123 | 0.011 | ns | ns | ns |
| Isovaleric Acid | 0.034 | 0.038 | 0.034 | 0.043 | 0.002 | ns | ns | ns |
| Valeric Acid | 0.037 | 0.040 | 0.038 | 0.038 | 0.003 | ns | ns | ns |

Probability of significance;
* = (p < 0.05),
** = (p < 0.01).

Pig offered LAM supplemented diets had improved Average Daily Gain (ADG) and gain to feed ratio (GFR) compared to pigs offered the unsupplemented diets. This positive response to LAM may be due to the reduced *E. coli* population in the gut of these pigs. Diets supplemented with LAM resulted in pigs having a reduced faecal *E. coli* population which resulted in reduced faecal DM and less diarrhoea (lower faecal score) during days 7-14, compared to pigs offered diets containing no LAM. Inclusion of LAM in the diet resulted in reduced *Enterobacteria* population in the gut of the pig. Thus the improved performance seen with pigs fed laminarin diets could be due to the associated antimicrobial properties of LAM, which may result in an improved health in water making it a rapidly fermentable carbohydrate source. *Lactobacillus* spp. have been reported to ferment a number of monosaccharides which included L-fucose. In the current study, it was found that the concentration of *Lactobacillus* spp. in the colon increased with the inclusion of FUC. Despite the increase in the *Lactobacilli* population, there was no dietary effect on VFA concentration or profiles. The quantity of VFA produced in the large intestine depends on the amount and composition of the substrate and on the microflora present (MacFarlane and MacFarlane, 2003). However, faecal VFA concentrations may not be a totally accurate way to demonstrate fermentation intensity in the large intestine.

The combination diets of FUC+LAM were most effective at reducing post weaning diarrhoea. This could be attributed to a number of reasons. Firstly, it could be due to an immune response from feeding the combination diets. Secondly, there was a numerical decrease in faecal *E. coli* numbers with the combination treatment. Pigs that express the symptoms of diarrhoea harbour massive numbers of haemolytic *E. coli*. Therefore, a reduction in the numbers of *E. coli* present in the gut would reduce the severity of diarrhoea and ultimately reduce piglet morbidity post weaning.

Overall, the reduction in faecal *E. coli* population and the increase in ADG and GFR suggest that LAM may provide a dietary means to improve gut health post weaning. However, a combination of LAM and FUC is more effective at reducing diarrhoea.

Example 5

Experimental Design and Animal Diets 21 pigs with an initial weight of 17.9±2.2 Kg were assigned to one of the 3 dietary treatments: (T1) control; (T2) basal diet+300 ppm LAM; (T3) basal diet+600 ppm LAM. Experimental feeding continued for 21 days ad libitum. Diets were formulated to have similar digestible energy (DE) (14.4 MJ/Kg) and ileal digestible lysine (12.5 g/Kg).

Microbial and Volatile Fatty Acid (VFA) Analysis

Post-slaughter, digestive tract was removed by dissection and digesta was removed from the ileum. Each digesta sample was serially diluted in maximum recovery diluent (MRD, Oxoid, Basingstoke, UK), and spread plated onto selective agars. *Bifidobacteria, Lactobacilli* and *Enterobacteria* species were isolated according to the methods described by Pierce et al. (2005). Digesta samples used to measure VFA concentration were collected from the caecum and the same location in the ileum and colon. VFA analysis was performed using gas liquid chromatography (GLC) according to the method described by Pierce et al., (2005).

Collection of Tissue Samples and Tissue Challenge Procedure

Ileal and colonic tissues were sampled from the same location as described for digesta samples. Excised tissues were emptied by dissecting them along the mesentery and rinsing them using sterile phosphate buffered saline (PBS) (Oxoid). Tissue sections 1 cm$^3$, which had been stripped of the overlying smooth muscle were cut from each tissue. Two sections from each tissue were placed in 1 ml of Dulbecco's Modified Eagle's Medium (DMEM) (Gibco), one in the presence of bacterial lipopolysaccharide (LPS) (Sigma Aldrich) at a concentration of 10 µg/ml. The other tissue sample was used as a control and incubated in sterile DMEM in the absence of LPS. Both challenged and unchallenged tissues were incubated at 37° C. for 90 minutes before being removed, blotted dry and weighed. Approximately 1-2 g of porcine ileum and colon tissues were cut into small pieces and collected in 15 ml of RNAlater® (Applied Biosystems, Foster City, Calif.). RNAlater® was removed before storing the samples at −80° C. until used for RNA extraction.

Preparation of Unchallenged Tissue for Quantitative Real Time PCR (qRT-PCR)

Ileal and colonic tissues was stabilised in RNAlater® solution and stored overnight at 4° C. The following day, RNAlater® was removed and samples were stored at −86° C. prior to RNA extraction.

RNA Extraction and cDNA Synthesis

Tissue samples for RNA extraction were removed from −86° C. and homogenised. 500 µl of lysis solution/2-ME was added to each sample and these were mechanically disrupted using one 5 mm stainless steel bead per sample. These were then placed in a Tissue Lyser (Qiagen) and lysates were homogenised for 3 mins and transferred to a GenElute Filtration Column (Sigma Aldrich) and RNA was extracted. 1 □g of total RNA was used for cDNA synthesis using oligo(dT)$_{20}$ primer in a final reaction volume of 20 µl with Superscript™ III First-Strand synthesis system for reverse transcriptase-polymerase chain reaction (RT-PCR) (Invitrogen Life Technologies, Carlsbad, Calif.). At the last step of cDNA synthesis, treatment with *E. coli* RNase H (Invitrogen Corp.) was performed to digest the remaining RNA/mRNA template, resulting in the production of the single-stranded cDNA template for subsequent qRT-PCR reactions.

Quantitative Real-Time PCR (qPCR) and Normalization of qPCR Data

All porcine primers for the cytokine genes interferon gamma (IFN-γ), interleukin-1α (IL-1α), IL-6, IL-8, IL-10, IL-17, tumour necrosis factor (TNF-α), the mucin genes (MUCs 1, 2, 4, 5AC, 12, 13 and 20) and three reference genes, β-actin (ACTB), Glyceraldehyde-3-phosphate dehydrogenase (GAPDH) and Peptidylprolyl isomerase A (PPIA), were designed using Primer Express™ (PE Applied Biosystems, Foster City, Calif.) and synthesised by MWG Biotech (Milton Keynes, UK). These reference genes were previously validated for use in porcine tissue and qPCR was then carried out on the cDNA using the ABI PRISM 7900HT Fast sequence detection system for 96-well plates (Applied Biosystems, Foster City, Calif.). All samples were prepared in duplicate using SYBR Green Fast PCR Master Mix (Applied Biosystems, Foster City, Calif.), cDNA as template and specific primers for the genes selected. For each reaction 5 µl cDNA, 1.2 µl (forward and reverse primer mix, 5 µM), 10 µl Fast SYBR Green PCR Master Mix (PE Applied Biosystems, Foster City, Calif.) was added and made up to a final volume of 20 µl. The two step PCR program was as follows: 95° C. for 10 minutes for 1 cycle followed by 95° C. for 15 seconds and 60° C. for 1 minute for 40 cycles. The raw Ct values for the reference genes were converted to relative quantities using the formula Q=E$^{\Delta Ct}$ where E is the PCR efficiency of the assay and $^{\Delta}$Ct is the value calculated for the difference between the lowest Ct value for each gene minus the Ct value of the sample in question. The relative quantities of the endogenous controls were then analysed for stability in geNorm (Vandesompele et al., 2002). The stability 'M' value generated by the geNorm application for the selected endogenous controls (ACTB, GAPDH and PPIA) indicated their suitability as endogenous controls for these intestinal samples. The geometric mean of the relative quantities for ACTB, GAPDH and PPIA (normalisation factor) was then calculated using geNorm. The relative quantities of each target gene were divided by the normalisation factor (obtained in geNorm) for that sample to give the final normalised relative expression.

Results

In this study, LAM from *Laminaria digitata* did not affect performance, nutrient digestibility or selected bacteria in the ileum, but it did decrease Enterobacteriaceae in the colon. Of particular interest was the impact of LAM on cytokine gene expression in the ileum and colon following in-vitro challenge with lipopolysaccharide (LPS).

Animal Performance and Nutrient Digestibility

There was no effect on performance (food intake, daily gain or food conversion ratio) or nutrient digestibility coefficients (DM, OM, ash, N or GE) with increasing LAM.

Microbiology and Volatile Fatty Acids (VFAs)

Increasing the level of LAM from 0-600 ppm had no effect on the *Bifidobacteria, Lactobacilli* or Enterobacteriaceae populations in the ileum (p>0.05). There was a decrease in Enterobacteriaceae populations with increasing LAM. The potential to reduce harmful Enterobacteriaceae strains, without influencing *Bifidobacteria* and *Lactobacilli* numbers is of great significance as pathogenic bacteria increase mortality rates . . . . In context, results indicate that the optimum LAM inclusion rate is 300 ppm.

TABLE 22

The effect of increasing LAM on selected microbial populations in the ileum, proximal and distal colon and total VFAs in the ileum, caecum and proximal colon of the pig.

| LAM | 0 ppm | 300 ppm | 600 ppm | SEM | Significance Linear | Quadratic |
|---|---|---|---|---|---|---|
| | ($Log_{10}$ CFU/g) | | | | | |
| | Ileum | | | | | |
| Bifidobacteria | 4.94 | 5.44 | 5.51 | 0.708 | ns | ns |
| Lactobacilli | 4.14 | 5.15 | 5.40 | 0.565 | ns | ns |
| Enterobacteriacae | 2.24 | 3.35 | 2.86 | 0.839 | ns | ns |
| | Colon | | | | | |
| Bifidobacteria | 7.37 | 7.29 | 7.46 | 0.365 | ns | ns |
| Lactobacilli | 7.89 | 8.16 | 8.19 | 0.221 | ns | ns |
| Enterobacteriacae | 5.42 | 3.87 | 4.24 | 0.358 | * | * |
| | Total VFAs | | | | | |
| Ileum | 10.47 | 14.84 | 14.26 | 2.60 | ns | ns |
| Caecum | 173.5 | 189.2 | 194.4 | 9.70 | * | ns |
| Colon | 185.4 | 146.4 | 161.8 | 13.79 | ns | ns |

Probability of significance:
* $P < 0.05$,
** $P < 0.01$,
*** $P < 0.001$,
ns = non-significant $P > 0.05$ There were no significant effects of increasing dietary inclusion levels of LAM on total VFAs, in the ileum or colon. There was a significant increase in total VFAs with increasing levels of LAM in the caecum (p<0.05), the main site of VFA production. There was no significant alteration in digesta pH recorded from any the intestinal region.

Cytokine Gene Expression

There were no effects of LAM in unchallenged ileum or colon tissue for any of the cytokines analysed. This overall lack of an effect on these inflammatory markers implies that the presence of LAM in the diet did not elicit any negative effects. To mimic the response of the ileal and colonic tissues of animals exposed to LAM to a microbial challenge, these tissues were subsequently incubated with LPS ex-vivo. While no effect was observed in the ileum, a significant challenge effect was observed for IL-6 and IL-8 gene expression in the colon of LPS-challenged tissue. LAM inclusion levels at 300 ppm lead to an increase in IL-6 expression (p<0.05), whilst a linear increase in IL-8 gene expression was observed (p<0.05). These data suggest that dietary LAM could enhance the pro-inflammatory response to microbial challenge. The potential benefit of this enhanced gene up-regulation of IL-6 and IL-8 cytokines following the LPS challenge are significant for the host as IL-6 is a pro-inflammatory cytokine that plays an important role in acute inflammation in the early immune response. Similarly the chemokine IL-8 also plays an important role in inflammation and is responsible for neutrophil recruitment and activation to the initial site of infection. While exposure to LAM alone did not stimulate pro-inflammatory cytokine production in the gastric mucosa, it enhanced the LPS induced pro-inflammatory cytokine production.

TABLE 23

The effect of increasing LAM from *Laminaria digitata* on the immune response in unchallenged ileum and colon tissues.

| LAM | 0 ppm | 300 ppm | 600 ppm | SEM | Significance Linear | Quadratic |
|---|---|---|---|---|---|---|
| | Ileum | | | | | |
| IFN-γ | 1.000 | 1.278 | 0.841 | 0.233 | ns | ns |
| IL-1α | 1.000 | 1.141 | 0.597 | 0.148 | ns | ns |
| IL-6 | 1.000 | 1.681 | 0.908 | 0.252 | ns | ns |
| IL-8 | 1.000 | 1.003 | 0.475 | 0.245 | ns | ns |
| IL-10 | 1.000 | 1.128 | 0.646 | 0.229 | ns | ns |
| TNF-α | 1.000 | 1.023 | 0.805 | 0.133 | ns | ns |
| | Colon | | | | | |
| IFN-γ | 1.000 | 1.217 | 1.148 | 0.286 | ns | ns |
| IL-1α | 1.000 | 0.716 | 0.851 | 0.144 | ns | ns |
| IL-6 | 1.000 | 1.579 | 1.788 | 0.434 | ns | ns |
| IL-8 | 1.000 | 1.245 | 1.137 | 0.224 | ns | ns |
| IL-10 | 1.000 | 1.029 | 0.843 | 0.285 | ns | ns |
| TNF-α | 1.000 | 1.400 | 1.446 | 0.301 | ns | ns |

Probability of significance:
* $p < 0.05$,
** $p < 0.01$,
*** $p < 0.001$,
ns = non-significant $p > 0.05$

TABLE 24

The effect of LAM from Laminaria digitata on immune response in the ileum and colon following an ex-vivo LPS tissue challenge.

| LAM | 0 ppm | 300 ppm | 600 ppm | SEM | Significance Linear | Quadratic |
|---|---|---|---|---|---|---|
| Ileum | | | | | | |
| IFN-γ | 1.000 | 0.927 | 1.098 | 0.223 | ns | ns |
| IL-1α | 1.000 | 1.072 | 1.039 | 0.161 | ns | ns |
| IL-6 | 1.000 | 1.352 | 1.143 | 0.266 | ns | ns |
| IL-8 | 1.000 | 1.186 | 0.903 | 0.362 | ns | ns |
| IL-10 | 1.000 | 1.198 | 1.076 | 0.160 | ns | ns |
| TNF-α | 1.000 | 0.819 | 0.921 | 0.108 | ns | ns |
| Colon | | | | | | |
| IFN-γ | 1.000 | 2.051 | 1.614 | 0.385 | ns | ns |
| IL-1α | 1.000 | 0.983 | 1.242 | 0.199 | ns | ns |
| IL-6 | 1.000 | 1.846 | 0.830 | 0.272 | * | * |
| IL-8 | 1.000 | 1.590 | 1.948 | 0.303 | * | — |
| IL-10 | 1.000 | 0.936 | 1.039 | 0.256 | ns | ns |
| TNF-α | 1.000 | 1.557 | 0.938 | 0.250 | ns | ns |

Probability of significance:
* $p < 0.05$,
** $p < 0.01$,
*** $p < 0.001$,
ns = non-significant $p > 0.05$ Mucin Gene Expression Dietary factors such as fibre, protein and anti-nutritional factors are known to directly influence the synthesis and secretion of mucin from goblet cells and the recovery of mucin in digesta (Montagne et al., 2004). All 7 mucin gene transcripts were reliably detected in the porcine colon but only five of the seven were accurately quantifiable in the ileum. An increase in MUC2 was observed in the ileum of pigs supplemented with LAM at 300 ppm (p=0.05) relative to the control animals. This increased MUC2 expression was not observed at the higher dietary inclusion level (600 ppm). LAM supplementation had no effect on the remaining detectable mucins (MUC4, MUC12, MUC13 and MUC20) in the ileum. In the colon, dietary supplementation with LAM at an inclusion level of 600 ppm, significantly increased MUC2 (quadratic; P<0.05) and MUC4 (quadratic; P<0.05) expression but had no effect on the expression of any of the remaining mucin genes at this site. Diets containing beta-glucans also affect the quality and quantity of mucin production of the jejunum, ileum, caecum and colon in the murine model (Deville et al., 2007).

TABLE 25

Effect of LAM from Laminaria digitata on mucin gene expression in ileum and colon.

| LAM | 0 ppm | 300 ppm | 600 ppm | Significance Linear | Quadratic |
|---|---|---|---|---|---|
| Ileum | | | | | |
| MUC2 | 1.000 | 0.000 | | * | * |
| MUC4 | 1.000 | 0.000 | | ns | ns |
| MUC12 | 1.000 | 0.000 | | ns | ns |
| MUC13 | 1.000 | 0.000 | | ns | ns |
| MUC20 | 1.000 | 0.000 | | ns | ns |
| Colon | | | | | |
| MUC1 | 1.000 | 0.902 | 1.270 | ns | ns |
| MUC2 | 1.000 | 0.726 | 1.207 | * | * |
| MUC4 | 1.000 | 0.981 | 1.351 | * | * |
| MUC5AC | 1.000 | 2.134 | 0.285 | ns | ns |
| MUC12 | 1.000 | 0.957 | 1.120 | ns | ns |
| MUC13 | 1.000 | 0.924 | 1.077 | ns | ns |
| MUC20 | 1.000 | 1.107 | 1.063 | ns | ns |

Probability of significance:
* $p < 0.05$,
** $p < 0.01$,
*** $p < 0.001$,
ns = non-significant $p > 0.05$ Optimum Inclusion Level 300 ppm LAM is sufficient to 'prime' the immune system in an ex-vivo LPS-challenge.

Example 6

Immune capacity can be modulated by nutritional interventions with LAM and/or FUC leading to a reduction in Porcine circovirus type 2 (PCV2) viral load in experimentally infected snatch farrowed pigs and ameliorating the effects of post-weaning multisystemic wasting syndrome (PMWS) in pigs.

Results

Immunofluorescent Detection of PCV2 Antigen in Tissues

PCV2 antigen was detected in tissue sections from necropsied animals (liver, lung, kidney, spleen, ILN, MLN) by immunofluorescence using PCV2-specific monoclonal antibody.

In the basal diet, 5 of 6 animals were euthanized.

In the basal diet+LAM and FUC treatment, one of six animals was euthanised.

In the basal diet with LAM and FUC and WPI, one of the six pigs was euthanised during of the experiment. Tissues from this animal contained high levels of PCV2 antigen. The remaining five animals appeared healthy at the end of the experiment. They had seroconverted and gained weight.

Determination of PCV2-Specific Antibody Titre

Referring to FIG. 1, there is shown the PCV2-specific antibody titre of sera, which was determined by IPMA.

Intra Group Analysis

Basal diet: 5 of 6 piglets gave a poor PCV2 antibody response and all had PCV2 antigen indicative of disease in analysed tissue sections. The remaining animal (Tag 10) seroconverted to a reasonable PCV2-specific antibody titre. This animal remained healthy throughout the duration of the experiment.

Basal diet+LAM and FUC treatment: 1 of 6 pigs had to be euthanised before the end of the experiment (Tag 30). This animal had the lowest PCV2-specific antibody titre of all animals in this group and PCV2 antigen levels in tissues were indicative of PCV2 associated disease. However, the antibody titre of this animal was higher than that of piglets that developed disease in Group 1.

Basal diet+with LAM and FUC+WPI: One of the six pigs was euthanized before the end of the experiment (Tag 26). All of the remaining five animals were healthy at the end of the experiment, had seroconverted and gained weight. Two animals (Tag 22 and 25) had high levels of PCV2 antigen in its tissues.

Inter Group Analysis

Figure 2:
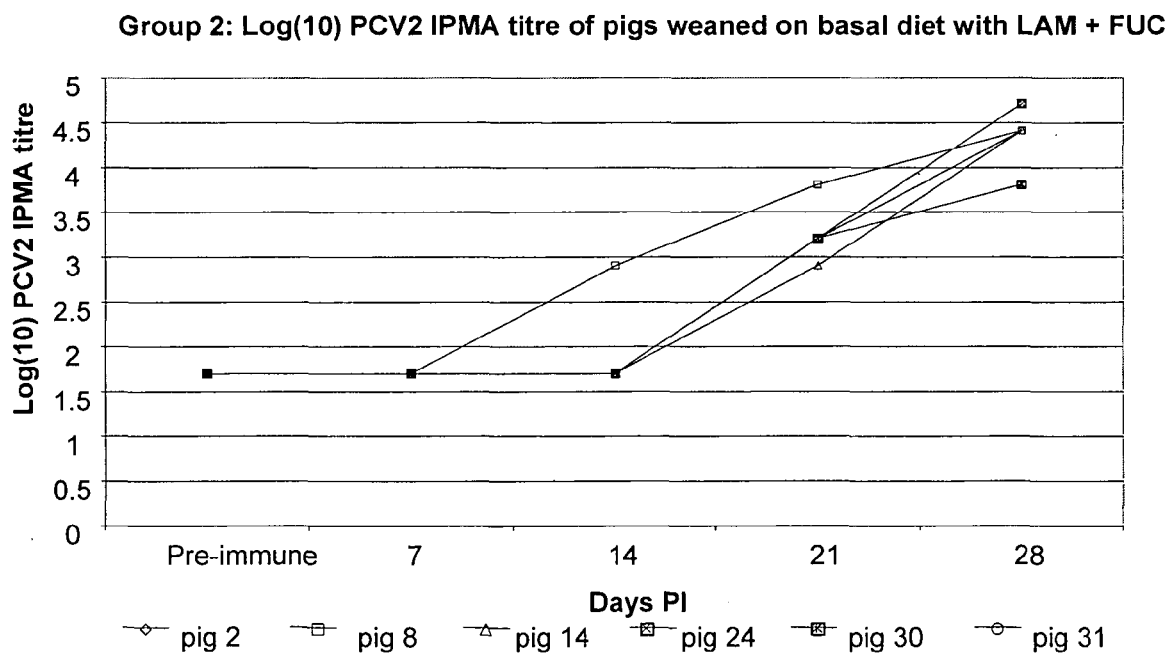
FIG. 2 illustrates PCV2-specific antibody titres of piglets fed a basal diet supplemented with LAM+FUC.
Figure 3:
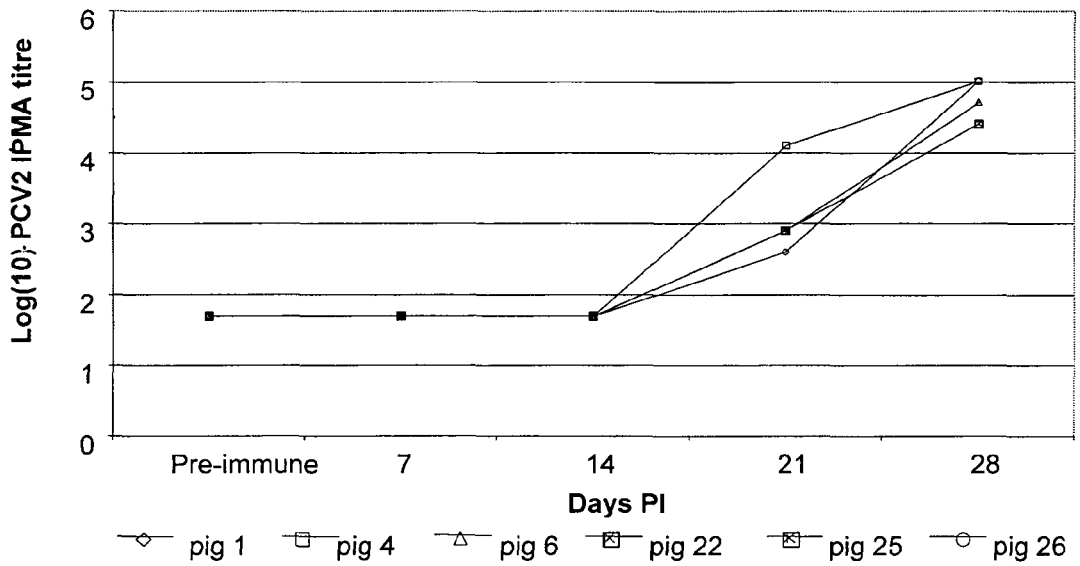
FIG. 3 illustrates PCV2-specific antibody titres of piglets fed a basal diet supplemented with LAM+FUC and WPI.

At 21 and 28 days post-infection (PI), the mean PCV2-specific antibody titre of animals in treatment 2 (+LAM and FUC; See FIG. 2) and 4 (+LAM and FUC+WPI, See FIG. 3) were significantly higher (p<0.05) than animals fed the basal diet and piglets fed the basal+WPI. These results suggest that LAM and FUC supplementation of pig feed, alone or in conjunction with WPI, boosts the humoral response of PCV2 infected pigs.

Lymphocyte Numbers

Figure 4:
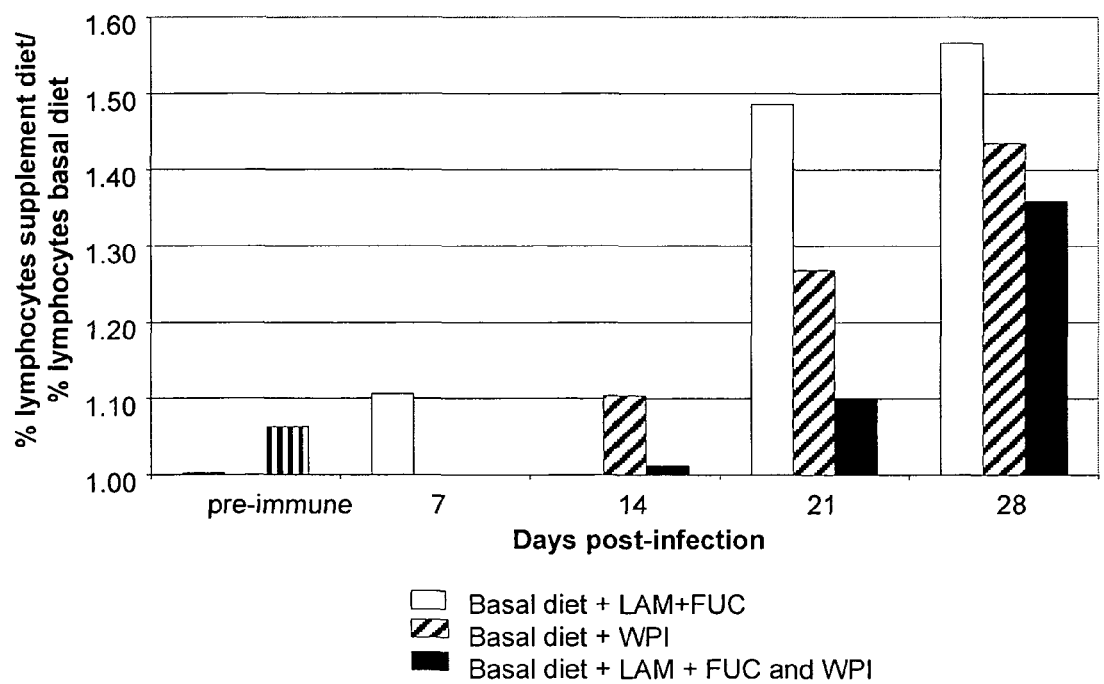
FIG. 4 illustrates the percentage lymphocyte population for piglets weaned onto different diets and subsequently challenged with PCV2 and PPV.
Figure 5:
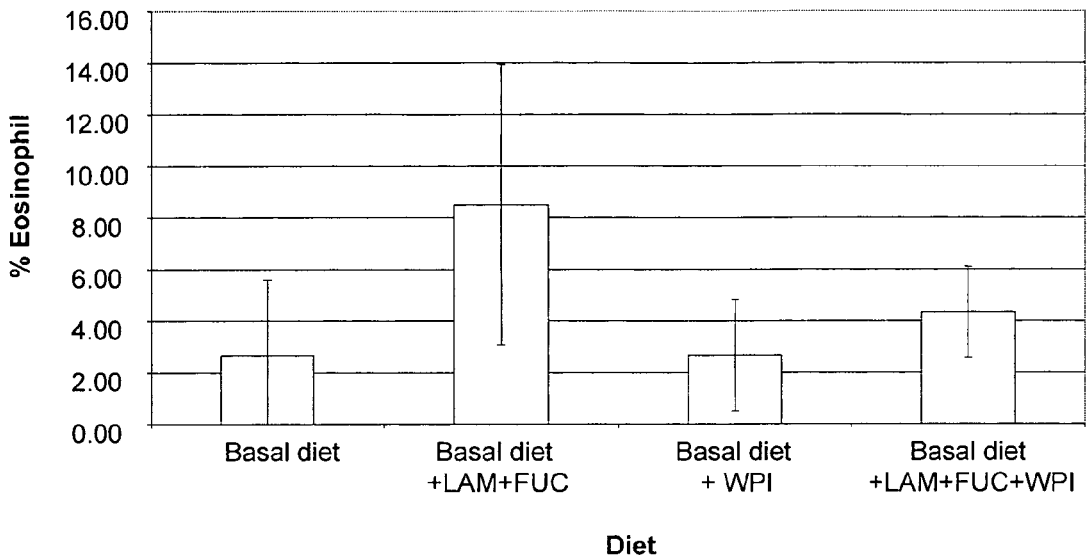
FIG. 5 illustrates the average percentage eosinophil population in piglets fed different diets and subsequently challenged with PCV2 and PPV (Day 14 PI)

Referring to FIG. 4, it can be seen that by day 28 post-infection (PI), the basal diet feed group had significantly lower percentage lymphocyte cell population than the three supplemented diets. Neither supplement was significantly different from each other. At 14 days PI, piglets fed a diet supplemented with LAM+FUC had significantly greater (p<0.05) percent eosinophils than all the other groups, as illustrated in FIG. 5. After this time, no significant difference was detected.

Analysis of Animal Weights

Figure 6:
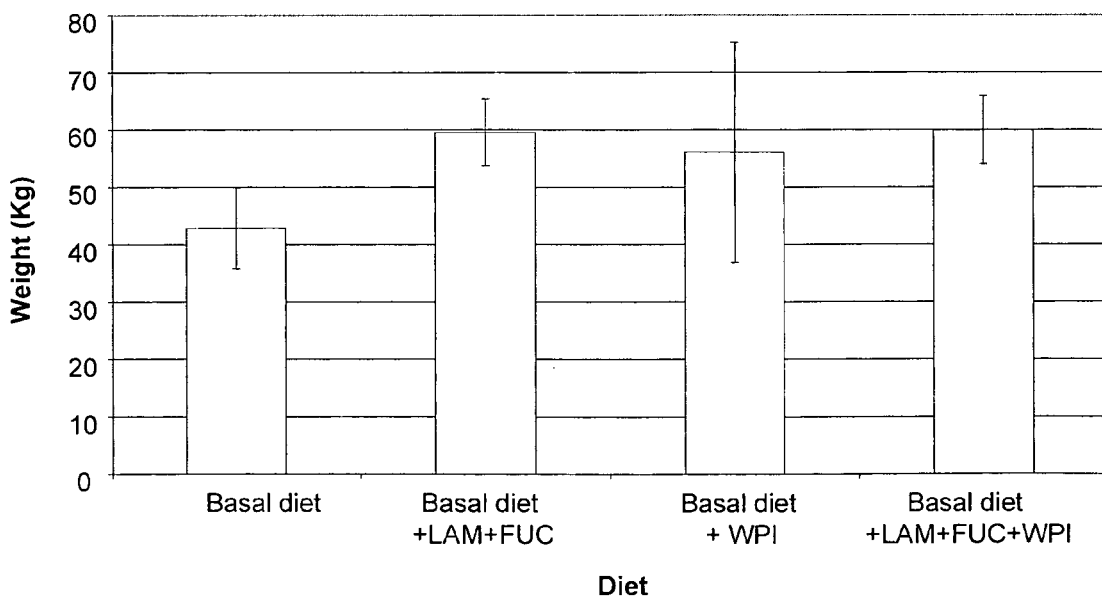
FIG. 6 illustrates the average terminal weight (Kg) of pigs weaned onto different diets and then challenged with PCV2 and PPV.

The weights of pigs were recorded weekly. With reference to FIG. 6, it can be seen that the average terminal weights of piglets in groups 2 (+LAM and FUC), 3 (+whey protein isolate) and 4 (+LAM and FUC+whey protein) were greater than those fed the basal diet. Animals in groups 2 and 4 were significantly heavier than piglets fed the basal diet.

Analysis of Animal Body Temperatures

Body temperatures were also monitored throughout the study. At 17 days PI, animals in group 3 (+whey protein isolate) and group 4 (+LAM and FUC and whey protein isolate) had significantly lower mean temperatures (38.33 and 38.02° C., respectively) than piglets fed the basal diet (39.82° C., p<0.05). No significant difference in mean body temperatures were observed between the individual feed groups at 24 days PI.

Analysis of Viral Shedding

Figure 7:
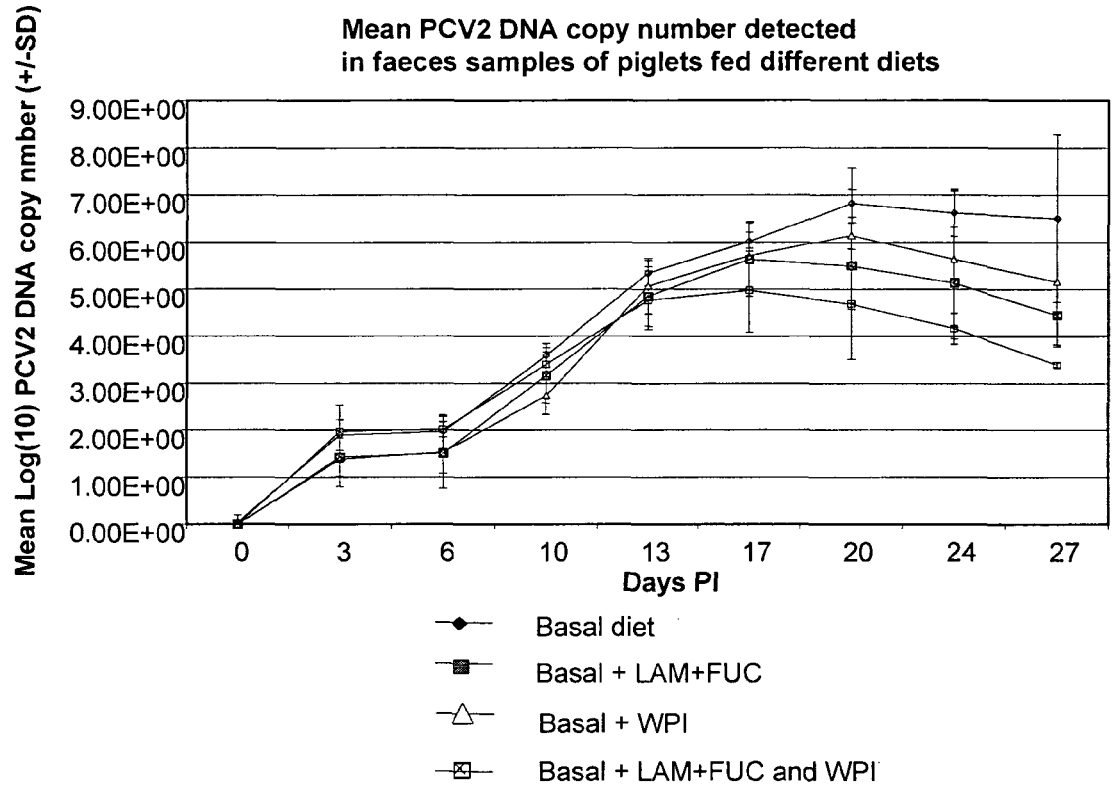
FIG. 7 illustrates the average PCV2 DNA copy number detected in faeces of piglets weaned onto different diets and subsequently challenged with PCV2 and PPV.
Figure 8:
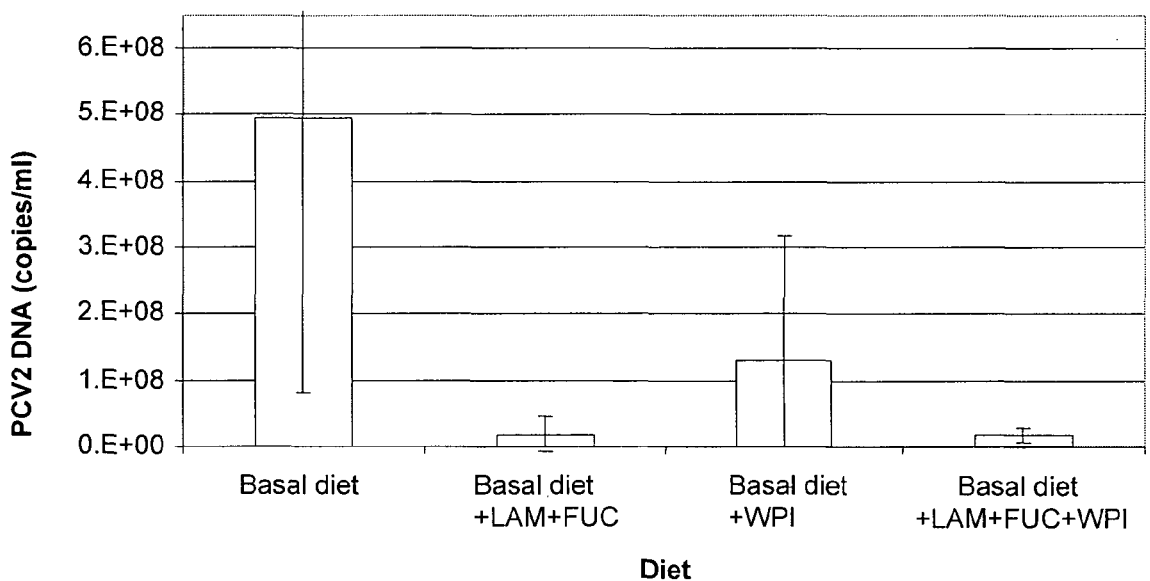
FIG. 8 illustrates PCV2 DNA copy number of pigs weaned onto different diets.

Quantitative PCR was performed on all faeces samples to estimate viral load and shedding. As illustrated in FIG. 7, by day 10 PI, the average PCV2 DNA copy number detected in animals in Group 3 (+whey protein isolate) was significantly lower (p<0.05) than the 3 other feed groups. On days 20 and 24 PI, piglets fed the LAM and FUC supplemented diet had significantly lower PCV2 DNA copies than piglets in Groups 1 and 3. Animals fed LAM and FUC and whey protein isolate contained significantly lower PCV2 DNA copy numbers than those in the basal diet (p<0.05). By day 27 PI, all supplemented diets had significantly lower copies of PCV2 DNA (p<0.05) than those on the basal diet. The lowest average PCV2 DNA copy number was detected in the faeces samples of piglets fed LAM+FUC, as seen in FIG. 8. These results indicate that supplementing pig feed with LAM+FUC, WPI, or both in combination led to a significant reduction in viral shedding of PCV2 under these experimental conditions.

TABLE 26

Immunofluorescence detection of PCV2 antigen in tissue sections.

| PM Number | Tag No | Group No | Liver | Lung | Kidney | Spleen | ILN | MLN | Disease status |
|---|---|---|---|---|---|---|---|---|---|
| Basal diet | | | | | | | | | |
| 07-11887 | 3 | 1 | 1+ | 3+ | 2+ | 3+ | 3+ | 2-3+ | Y |
| 07-11872 | 5 | 1 | 3+ | 4+ | 2-3 | 4+ | 1+ | 2+ | Y |
| 07-11893 | 7 | 1 | 2-3+ | 4+ | 2-3+ | 3+ | 4+ | 4+ | Y |
| 07-11894 | 10 | 1 | 2+ | 3-4+ | 1-2+ | 3+ | No tissue | 2-3+ | Y |
| 07-11881 | 20 | 1 | 1+ | 1+ | 1-2+ | 1+ | 2+ | 2-3+ | N |
| 07-11889 | 35 | 1 | 2+ | 2-3+ | 1-2+ | 1-2+ | 3+ | 3+ | Y |
| Basal diet + 1 g/Kg LAM and FUC | | | | | | | | | |
| 07-11888 | 2 | 2 | +/− | +/− | 1+ | 1+ | 2+ | 1-2+ | N |
| 07-11886 | 8 | 2 | −ve | −ve | +/− | 1-2+ | 1+ | 1-2+ | N |
| 07-11871 | 14 | 2 | +/− | +/− | 1+ | 1+ | 1-2+ | 1+ | N |
| 07-11878 | 24 | 2 | −ve | −ve | +/− | 1+ | 1+ | 1-2+ | N |
| 07-11890 | 30 | 2 | 2-3+ | 3+ | 2+ | 2-3+ | 4+ | 3+ | Y |
| 07-11882 | 31 | 2 | +/− | +/− | 1+ | 1+ | 1-2+ | 2+ | N |
| Basal diet + 80 g/Kg whey protein isolate | | | | | | | | | |
| 07-11869 | 9 | 3 | 1+ | 1-2+ | 1+ | 2+ | 3+ | 3-4+ | Y |
| 07-11884 | 15 | 3 | 2-3+ | 3-4+ | 3+ | 3+ | 3-4+ | 3-4+ | Y |
| 07-11863 | 19 | 3 | 1+ | 1+ | 2+ | 1+ | 2+ | 3+ | Y |
| 07-11892 | 27 | 3 | 2-3+ | 4+ | 2+ | 2-3+ | 4+ | 3+ | Y |
| 07-11859 | 29 | 3 | −ve | +/− | 2+ | 2+ | 3+ | 3-4+ | Y |
| 07-11858 | 38 | 3 | −ve | −ve | −ve | +-1+ | 1+ | 1+ | N |
| Basal diet + 1 g/Kg LAM and FUC + 80 g/Kg whey protein isolate | | | | | | | | | |
| 07-11861 | 1 | 4 | +/− | + | 1+ | + | 2-3+ | 1-2+ | N |
| 07-11870 | 4 | 4 | −ve | −ve | 1-2+ | 1+ | 2+ | 2+ | N |
| 07-11867 | 6 | 4 | −ve | −ve | 1-2+ | +/− | 1-2+ | 2+ | N |
| 07-11862 | 22 | 4 | +/− | + | 1+ | 1-2+ | 2-3+ | 3+ | Y |
| 07-11860 | 25 | 4 | 2+ | 3+ | 3+ | 2-3+ | 4+ | 4+ | Y |
| 07-11895 | 26 | 4 | 2-3+ | 3-4+ | 2+ | 3+ | No tissue | 2+ | Y |

Scores ≥3+ = high level of viral antigen indicative of PCV2-associated disease.

Cytokine PCR Results

Cytokine mRNA for IL-2, TNF-α and IL-4 were quantified using an established two-step reverse transcription PCR (rt-PCR) assay. Results indicated that there were no significant differences in the profile of these cytokines between the different feed treatments.

Quantification of PCV2 DNA in Tissue Homogenate

Tissue homogenate pools (10% w/v) were prepared from the liver, lung, spleen, kidney, mesenteric and inguinal lymph nodes of each animal. PCV2 DNA was quantified using an established quantification PCR method (qPCR). The highest amounts of PCV2 DNA were detected in animals that received the basal diet (Group 1). Pigs fed the diet supplemented with WPI (Group 3) also had higher quantities of PCV2 DNA than groups that received the basal diet supplemented with either LAM+FUC (Group 2) or LAM+FUC in combination with WPI (Group 4). These results compare favourably with the levels of the immunofluorescence-based detection of PCV2 antigen in the animal tissues. The least amount of PCV2 antigen was detected in animals fed a diet supplemented with LAM+FUC alone or in conjunction with WPI compared to the other two groups (i.e. basal/basal+WPI).

This invention reduces Porcine circovirus type 2 (PCV2) viral load in experimentally infected snatch farrowed pigs and ameliorates the effects of post-weaning multisystemic wasting syndrome (PMWS) in pigs.

BIBLIOGRAPHY

Association of Analytical Chemicals (1995). Official Methods of Analysis, 16$^{th}$ edition, Association of Official Chemists, Washington D.C., USA.

Close, W. H. (1994). Feeding new genotypes: establishing amino acid/energy requirements. In Principals of Pig Science (ed. D. J. A. Cole, J. Wiseman and M. A. Varley): 123-140. Nottingham University Press.

Deville, C; Damas, J., Forget, P; Dandrifosse, G. and Peulen, O (2004). Laminarin in the dietary fibre concept. Journal of the Science of Food and Agriculture. 84; 1030-1038.

Deville, C; Gharbi, M.; Dandrifosse, G. and Peulen, O (2007). Study of the effects of laminarin, a polysaccharide from seaweed on gut characteristics. Journal of the Science of Food and Agriculture 87: 1717-1725.

Gardiner, G. E., Campbell, A. J., O'Doherty, J. V., Pierce, E., Lynch, P. B., Leonard, F. C., Stanton, C., Ross, R. P. and Lawlor, P. G. (2008). Effect of *Ascophyllum nodosum* extract on growth performance, digestibility, carcass characteristics and selected intestinal microflora populations of grower-finisher pigs. *Anim. Feed. Sci. Technol.* 141:259-273.

Hojberg, O., Canibe, N., Knudsen, B and Jensen, B. B., 2003. Potential rates of fermentation in digesta from the gastrointestinal tract of pigs: Effect of feeding fermented liquid feed. Appl. Environ. Micro. 69, 408-418.

Huber, R. E. & Hurlburt, K. L. (1984). *Escherichia coli* growth on lactose requires cycling of beta-galactosidase products into the medium. Canadian Journal of Microbiology, 30, 411-415.

Ilsley, S. E.; Miller, H. M. and Kamel, C. (2005). Effects of dietary quillaja saponin and curcumin on the performance and immune status of weaned piglets. *Journal of Animal Science* 83: 82-88.

Klasing K. C. and Barnes D. M. (1988). Decreased amino acid requirements of growing chicks due to immunologic stress. *Journal of Nutrition* 118:1158-1164.

Kogan G and Kocher A 2007. Role of yeast cell wall polysaccharides in pig nutrition and health protection. Livestock Science, 10th Int. Sym. Dig. Phy. in Pigs, Denmark 2006, Part 2 109, 161-165 Krakowskia, L.; Krzyanowskia, J.; Wronaa, Z. and Siwickib, A. K. (1999). The effect of nonspecific immunostimulation of pregnant mares with 1,3/1,6 glucan and levamisole on the immunoglobulins levels in colostrum, selected indices of nonspecific cellular and humoral immunity in foals in neonatal and postnatal period. *Veterinary Immunology and Immunopathology.* 68 (1), 1-11.

Lynch, M. B.; Sweeney, T.; Callan, J. J. and O'Doherty, J. V. (2007). Effects of increasing the intake of dietary β-glucans by exchanging wheat for barley on nutrient digestibility, nitrogen excretion, intestinal microflora, volatile fatty acid concentration and manure ammonia emissions in finishing pigs. *Animal* 1(6): 812-819.

Lynch, M. B., Sweeney, T., Callan, J. J., O'Sullivan, J. T. and O'Doherty, J. V. (2009). The effect of dietary *Laminaria*-derived laminarin and fucoidan on nutrient digestibility, nitrogen utilisation, intestinal microflora and volatile fatty acid concentration in pigs. J. Sci. Food. Agric. 90:430-437.

Macfarlane, G. T., Hay, S., Macfarlane, S. & Gibson, G. R. (1990). Effect of different carbohydrates on growth, polysaccharide and glycosidase production by bacteriodes ovarus, in batch and continuous culture. Journal of Applied Bacteriology, 68, 179-187.

Macfarlane, S. and Macfarlane, G. T. (2003). Regulation of SCFA production. Proc. Nutr. Soc. 2003 62, 67-72.

Mackie, R. I., Stroot, P. G. and Varel, V. H. (1998). Biological identification and biological origin of key odour compounds in livestock waste. *Journal of Animal Science.* 76: 1331-1342.

Mackie R I; Sghir A; Gaskins H R (1999). Developmental microbial ecology of the neonatal gastrointestinal tract. *The American Journal of Clinical Nutrition* 69 (5):1035S-1045S.

Mortensen, P. B., Holtug, K. And Rasmussen, H. S. 1987. Short chain fatty acid production from mono and disaccharides in a faecal incubating system: implications for colonic fermentation of dietary fibre in humans. *Nutrition Journal* 118: 321-324.

O'Connell, M., Callan, J. J., Byrne, C., Sweeney, T and O'Doherty, J. V. 2005. The effect of cereal type and exogenous enzyme supplementation in pig diets on nutrient digestibility, intestinal microflora, volatile fatty acid concentration and manure ammonia emissions from pigs. *Animal Science* 81: 357-364.

O'Doherty, J. V., S, N. C., Callan, J. J. & McCarthy, P. (2004). The interaction between lactofeed level and soyabean meal on growth performance of weanling pigs. Anim. Sci. 78, 419-427.

O'Doherty, J. V., Nolan. C. S., Mccarthy, P. C. (2005a). Interaction between lactose levels and antimicrobial growth promoters on growth performance of weanling pigs. J. Sci. Food Agricult. 85, 371-380.

O'Doherty, J. V., Pierce, K. M. & Kenny, D. A. (2005b). Fermentable fibre and gut health in non- and pre-ruminants. IN GARNSWORTHY, P. C. & WISEMAN, J. (Eds.) Recent Adv. Anim. Nutr.

Partridge, G. G and Gill, B. P., 1993. New approaches with pig weaner diets. In: Wiseman, J. and Garnsworthy, P. C. (Eds), Recent Advances in Animal Nutrition. Nottingham University Press, U.K, pp. 221-248.

Pie S., Lalles J. P., Blazy F., Laffitte J., Seve B., Oswald I. P. (2004): Weaning is associated with an upregulation of expression of inflammatory cytokines in the intestine of piglets. *Journal of Nutrition.* 134: 641-647.

Pierce, K. M., Callan, J. J., Mccarthy, P. & O'Doherty, J. V. (2005a). Performance of weanling pigs offered low or high lactose diets supplemented with avilamycin or inulin. Anim. Sci. 80, 313-318.

Pierce, K. M.; Sweeney, T.; Brophy, P. O.; Callan, J. J.; Fitzpatrick, E.; McCarthy, P. and O'Doherty, J. V. (2006a). The effect of lactose and inulin on intestinal morphology, selected microbial populations and volatile fatty acid concentration in the gastrointestinal tract of the weanling pig. *Animal Science* 82, 311-318.

Pierce, K. M.; Sweeney, T.; Callan, J. J.; Byrne, C.; McCarthy, P. and O'Doherty, J. V. (2006b). The effect of inclusion of a high lactose supplement in finishing diets on nutrient digestibility, nitrogen excretion, volatile fatty acid concentrations and ammonia emission from boars. *Animal Feed Science and Technology* 125, 45-60.

Pollmann, D. S., Danielson, D. M. and Peo, E. R., (1980). Effect of *Lactobacillus acidophilus* on starter pigs fed a diet supplemented with lactose. J. Anim. Sci. 51, 638-644.

Porter, M. G. and Murray, R. S. (2001). The volatility of components of grass silage on oven drying and the interrelationship between dry-matter content estimated by different analytical methods. *Grass and Forage Science* 56: 405-411.

Rasmussen, H. S.; Holtug, K. and Mortensen, P. B. (1988). Degradation of amino acids to short chain fatty acids in humans. An in-vitro study. *Scandinavian Journal of Gastroenterology*. 23: 178-182.

Read, S. M.; Currie, G. and Bacic, A. (1996). Analysis of the structural heterogeneity of laminarin by electrospray-ionisation-mass spectrometry. *Carbohydrate Research* 281: 187-201.

Reilly, P., J. V. O'Doherty, K. M. Pierce, J. J. Callan, J. T. O'Sullivan, and T. Sweeney (2008). The effects of seaweed extract inclusion on gut morphology, selected intestinal microbiota, nutrient digestibility, volatile fatty acid concentrations and the immune status of the weaned pig. Animal 2:1465-1473.

Rooke, J A; Carranca, C; Bland, I M; Sinclair, A G; Ewen, M; Bland, V C (2003). Relationships between passive absorption of immunoglobulin G by the piglet and plasma concentrations of immunoglobulin G at weaning. *Livestock Production Science* 81, 223-234.

Swann Report (1969). Joint Committee on the Use of Antibiotics in Animal Husbandry and Veterinary Medicine. Report. HMSO, London SAS (1985). Statistical Analysis Systems. SAS Institute Inc., North Carolina, USA.

Topping, D. L. and Clifton, P. M., (2001). Short-chain fatty acids and human colonic function: roles of resistant starch and non-starch polysaccharides. *Physiological Reviews* 81: 1031-1064

The invention claimed is:

1. A method for improving or maintaining the health, structure, function, immunity or performance of the progeny of a maternal animal or human or treating or preventing disorders in structure or function or immunity in the progeny of a maternal animal or human to levels equivalent to or greater than those achieved by direct administration to each individual progeny at weaning or later, the method comprising administering a composition comprising at least one Beta-glucan, and optionally at least one fucan to the maternal animal or human, wherein the composition is administered to the maternal animal or human in an amount such that about 2-50 milligrams of Beta-glucan per kilogram of body weight is administered to the maternal animal or human.

2. The method according to claim 1, wherein the at least one Beta-glucan is beta (1→3, 1-4) glucan or beta (1→3, 1→6) glucan.

3. The method according to claim 1, wherein the at least one Beta-glucan is laminarin.

4. The method according to claim 1, wherein the at least one fucan is an alpha-fucan.

5. The method according to claim 1, wherein the at least one Beta-glucan and/or the at least one fucan is isolated from a brown macroalga of the class Phaeophycea.

6. The method according to claim 1, wherein the at least one Beta-glucan and/or the at least one fucan is isolated from a red alga selected from Florideophyceae.

7. The method according to claim 1, wherein the composition is administered to the maternal animal or human perinatally and/or prenatally, and/or postnatally.

8. The method according to claim 1, wherein the composition is administered daily to the maternal animal or human.

9. The method according to claim 1, wherein the composition is administered to the maternal animal or human in an amount such that about 2-40 milligrams of fucan per kilogram of body weight is administered to the maternal animal or human.

10. The method according to claim 1, wherein the maternal animal or human is a monogastric animal selected from the group consisting of pigs, poultry, fish, cats, dogs and humans and/or the animal is a hind-gut fermenter selected from the group consisting of horses and rabbits.

11. The method according to claim 9, wherein the composition is administered daily to the maternal animal or human.

12. The method according to claim 1, wherein the disorder of structure or function is treated or prevented by altering immunological function and/or immunological profile and/or altering immune gene expression and/or expression or secretion of signaling proteins and/or altering the expression of intra-cellular and/or extra-cellular receptors.

13. The method according to claim 1, wherein immunological function and/or immunological profile is improved by altering leukocyte numbers and/or leukocyte function and/or leukocyte phenotype and/or leukocyte trafficking and/or leukocyte distribution and/or cytokine gene expression and/or cytokine secretion and/or cytokine receptor expression.

14. The method according to claim 13, wherein leukocyte numbers are reduced and/or phagocytic activity is increased.

15. The method according to claim 13, wherein the cytokine is selected from pro-inflammatory and/or anti-inflammatory cytokines.

16. The method according to claim 1, wherein the disorder of structure or function in the progeny is a chronic disease selected from the group consisting of Crohn's disease, Irritable Bowel syndrome, and Colitis.

17. The method according to claim 1, wherein the disorder of structure or function in the progeny is an autoimmune disease.

18. The method according to claim 1, wherein the disorder of structure or function in the progeny is an inflammatory disease.

19. The method according to claim 1, wherein the disorder of structure or function in the progeny is an atopic disease.

20. The method according to claim 1, wherein the disorder of structure or function in the progeny is prevented or its symptoms and complications are reduced by increasing the concentration of immunoglobulin in the colostrum or milk of a maternal animal or human.

21. The method according to claim 1, wherein the disorder of structure or function in the progeny is prevented or its symptoms and complications are reduced by decreasing bacterial infection and/or decreasing viral infection.

22. The method according to claim 1, wherein the disorder of structure or function in the progeny is prevented or its symptoms and complications are reduced by increasing the expression of mucins.

23. The method according to claim 1, wherein the disorder of structure or function in the progeny is one which gives rise to wasting away of muscle and/or fat tissue.

24. The method according to claim 1, wherein the disorder of structure or function in the progeny is prevented or its symptoms and complications are reduced by decreasing infection or load of viral pathogen.

25. The method according to claim 24, wherein the viral pathogen is a non-enveloped virus.

26. The method according to claim 1, wherein the disorder of structure or function in the progeny is prevented or its symptoms and complications are reduced by increasing the production of straight-chain volatile fatty acids and/or reduction of branched-chain fatty acids.

27. The method according to claim 1, wherein the at least one fucan is fucoidan.

28. The method according to claim 1, wherein the at least one Beta-glucan and/or at least one fucan is derived from at least one family selected from the group consisting of Laminariaceae, Fucaceae and Lessoniaceae.

29. The method according to claim 1, wherein the at least one Beta-glucan and/or the at least one fucan is selected from at least one species from the group consisting of *Ascophyllum* species; *Laminaria* species and *Sargassum* species.

30. The method according to claim 1, wherein the at least one Beta-glucan is derived from a species of fungi.

31. The method according to claim 1, wherein the at least one Beta-glucan is derived from yeast.

32. The method according to claim 1, wherein the at least one Beta-glucan is derived from *Saccharomyces cerevisiae*.

33. The method according to claim 1, wherein the disorder of structure or function in the progeny is selected from the group consisting of psoriasis, rheumatoid arthritis, psoriatic arthritis, atopic dermatitis and juvenile idiopathic arthritis.

34. The method according to claim 1, wherein the disorder of structure or function in the progeny is prevented or its symptoms and complications are reduced by decreasing infection selected from the group consisting of *Escherichia coli* infection, *Campylobacter* infection, *Salmonella*, porcine circovirus infection and PCV-2 infection.

35. The method according to claim 1, wherein the at least one Beta-glucans is derived by approaches which include synthetic chemistry and biotechnology-related approaches.

36. The method according to claim 1, wherein the at least one fucan is derived by approaches which include synthetic chemistry and biotechnology-related approaches.

37. The method according to claim 1, wherein administration of the composition to the maternal animal or human confers benefits to a single progeny from the maternal animal or human.

38. The method according to claim 1, wherein administration of the composition to the maternal animal or human confers benefits to multiple birth progeny from the maternal animal or human.

39. The method according to claim 1, wherein administration of the composition to the maternal animal or human confers benefits to multiple birth progeny such that 2 or more progeny from the maternal animal or human are affected.

40. The method according to claim 24, wherein the viral pathogen is an enveloped virus.

41. The method according to claim 24, wherein the viral pathogen is selected from the group consisting of porcine circovirus and avian influenza.

* * * * *